United States Patent
Zhao et al.

(10) Patent No.: US 7,927,634 B2
(45) Date of Patent: Apr. 19, 2011

(54) **COMPOSITIONS AND METHODS FOR TREATING ANGIOGENESIS-RELATED DISEASES, WOUNDS AND COSMETIC USE OF COMPONENTS OF *ANGELICA SINENSIS*, AND METHODS OF PREPARATION THEREOF**

(75) Inventors: Hui Zhao, Santa Paula, CA (US); Krzysztof Bojanowski, Santa Paula, CA (US); Fariba Aria, Cupertino, CA (US); Reza Mortezaei, Cupertino, CA (US)

(73) Assignee: Sunny Biodiscovery, Inc., Santa Paula, CA (US)

( * ) Notice: Subject to any disclaimer, the term of this patent is extended or adjusted under 35 U.S.C. 154(b) by 0 days.

(21) Appl. No.: 12/758,863

(22) Filed: Apr. 13, 2010

(65) Prior Publication Data

US 2010/0255069 A1 Oct. 7, 2010

Related U.S. Application Data

(63) Continuation of application No. 10/948,590, filed on Sep. 24, 2004, now abandoned.

(51) Int. Cl.
*A61K 36/00* (2006.01)
*A61L 15/16* (2006.01)

(52) U.S. Cl. .................... 424/725; 424/446; 424/447

(58) Field of Classification Search .................. None
See application file for complete search history.

(56) References Cited

U.S. PATENT DOCUMENTS

| | | | |
|---|---|---|---|
| 6,468,553 B1 | 10/2002 | Sheu et al. | |
| 7,303,772 B2 * | 12/2007 | Olalde Rangel | 424/728 |
| 2008/0021421 A1 * | 1/2008 | Sun | 604/307 |

FOREIGN PATENT DOCUMENTS

CN 1072088 5/1993

OTHER PUBLICATIONS

Homan, Royal Pharm. Society of Great Britain, 2002. "Drug Preparation and Extraction."

* cited by examiner

*Primary Examiner* — Christopher R. Tate
(74) *Attorney, Agent, or Firm* — Nixon Peabody LLP

(57) ABSTRACT

Compositions and methods for treating angiogenesis-related diseases and for skin care in mammals is disclosed that includes, as an active pharmaceutical agent, an effective amount of purified extract from *Angelica sinensis*, or a fraction or a lyophilizate thereof, or one or more active component contained in said extract.

15 Claims, 12 Drawing Sheets

0h

24h

48h

Figure 1:
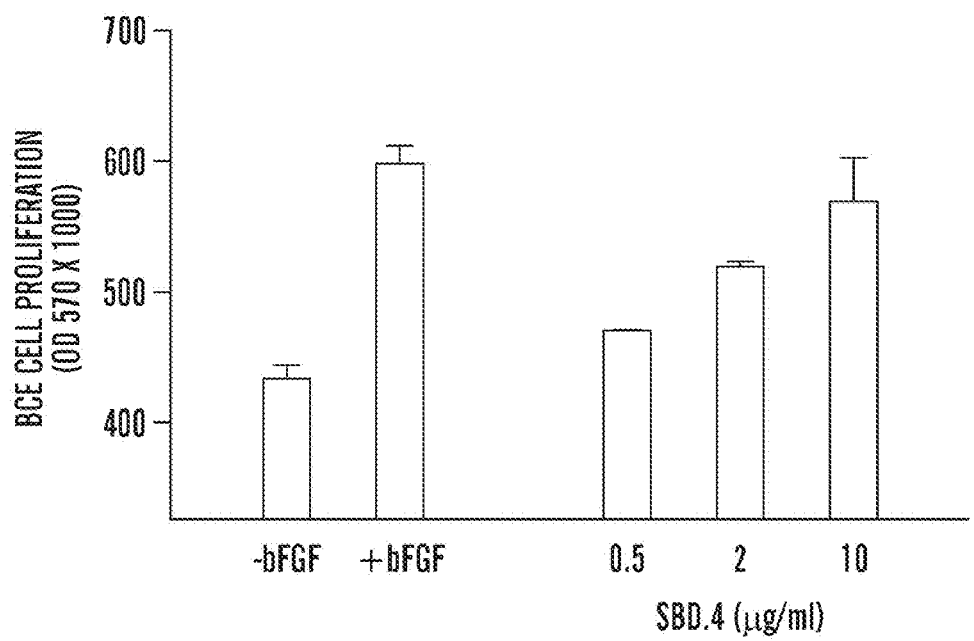

COMPOSITIONS AND METHODS FOR TREATING ANGIOGENESIS-RELATED DISEASES, WOUNDS AND COSMETIC USE OF COMPONENTS OF *ANGELICA SINENSIS*, AND METHODS OF PREPARATION THEREOF

CROSS-REFERENCE TO RELATED APPLICATIONS

This application is a continuation application of U.S. patent application Ser. No. 10/948,590 filed on Sep. 24, 2004, which claims the benefit of priority under 35 U.S.C. §119(e) of U.S. Provisional No. 60/505,174 filed Sep. 22, 2003, the contents of which are incorporated herein by reference in its entirety.

BACKGROUND OF THE INVENTION

Angiogenesis (the grow or assembly or formation of blood vessels) is an essential process during embryogenesis and pre-adult physiological development. In adults, angiogenesis is an important beneficial reparative process in wound healing, menstrual cycle, and bone repair, as well as in the recovery from stroke, peptic ulcers and certain cardiovascular diseases. Preservation of healthy network of dermal blood vessels is also essential for skin health and delaying skin ageing process. Several endogenous angiogenesis stimulators or factors have been reported that include basic fibroblast growth factor (bFGF) and its fragments, vascular endothelial growth factors (VEGF) and their fragments, interleukin 1 alpha and others. Therapeutic administration of some of these factors has been described to be useful and beneficial in many of the aforementioned physiological conditions. For example, basic fibroblast growth factor (bFGF) has been reported to improve quality of life as assessed by Seattle Angina Questionnaire and improve exercise tolerance as assessed by treadmill exercise testing in patients ischemic heart disease not amenable to treatment with coronary artery bypass graft (CABG) or percutaneous transluminal coronary angioplasty (PTCA) (Laham et al., 2000). Moreover, bFGF was shown by magnetic resonance imaging (MRI) to increase regional wall thickening and to reduce the extent of the ischemic area at all time points compared with baseline. However, effective angiogenesis stimulators with low side effect still represent a therapeutic gap even today, since there are no angiogenesis stimulators available that are approved by FDA for broad human use.

Furthermore, conditions, such as wounds, photodamaged and aged skin require activation of proliferation of several cell types, including endothelial cells and fibroblasts.

In our invention, we teach that an aqueous extract from *Angelica sinensis* or a fraction or a lyophilizate thereof, or one or more active components contained in said extract, stimulates endothelial cell growth in vitro, vessel-like structure formation in vitro and angiogenesis in vivo, indicating that *Angelica sinensis* or the compositions thereof may be useful for treating a vast array of pathologic conditions which require stimulation of angiogenesis, such as cardiovascular diseases, stroke, bone loss, peptic ulcers and skin wounds. It also indicates that SBD.4 may delay the process of dermal ageing by maintaining healthy irrigation of the skin and find use in the cosmetic products as active ingredients.

Furthermore, we teach that SBD.4 stimulates the proliferation of dermal fibroblasts. Proliferation of dermal fibroblasts is necessary for wound closure. Several angiostimulators were shown to enhance fibroblast growth (e.g. bFGF). Fibroblast cells are the major component of the dermis layer of the skin. They secrete collagens and other extracellular matrix components, which determine the elasticity, thickness and resilience of the skin. Therefore, natural products, which can support fibroblast metabolism and survival, but which at least minimally stimulate cancer cells, are of major interest as, for example, wound healing and cosmetic active ingredients.

Furthermore, we teach that SBD.4 not only protects and enhances microcirculation and dermal fibroblast growth, but also stimulates collagen I levels in fibroblast culture medium. Collagen I is a key component of extracellular matrix in the skin. In aged and damaged skin, collagen I levels are decreased due to the lower amount and quality of dermal fibroblasts. Collagen I output is also an important part of the wound healing process.

SUMMARY OF THE INVENTION

This invention describes a new use of a water extract (also referred here to as crude aqueous extract) from the roots of *Angelica sinensis* (family of Umbelliferae; also known as dang gui, dan gui, dong quai, tang kuei, Chinese angelica) or a fraction or a lyophilizate thereof, or one or more active components contained in said extract, this use being to stimulate endothelial cell proliferation, angiogenesis, and fibroblast growth. The abovementioned aqueous extract or a fraction or a lyophilizate thereof, or one or more active components contained in said extract which stimulate endothelial cell proliferation, angiogenesis, and fibroblast growth, also referred here to as SBD.4, or SBD.4 bioactive material is also known as ProDermin and Angiogent.

The stimulation of angiogenesis and fibroblast growth by SBD.4 may be a valuable treatment for cardiovascular and other ischemic diseases, bone loss, stroke, peptic ulcers, wounds, for personal care (such as skin, lip, hair care), and for other conditions where the stimulation of fibroblast growth and/or angiogenesis, or protection of vascular networks is beneficial.

BRIEF DESCRIPTION OF THE INVENTION

FIG. 1. Stimulatory effect of SBD.4 purified by the means of DEAE-cellulose on proliferation of bovine endothelial cells, as compared with a potent angiogenesis stimulator bFGF (1 ng/ml). −bFGF illustrates BCE proliferation in the absence of bFGF and SBD.4. The final concentrations of SBD.4 tested are 0.5 µg/ml and 10 µg/ml.

Figure 2:
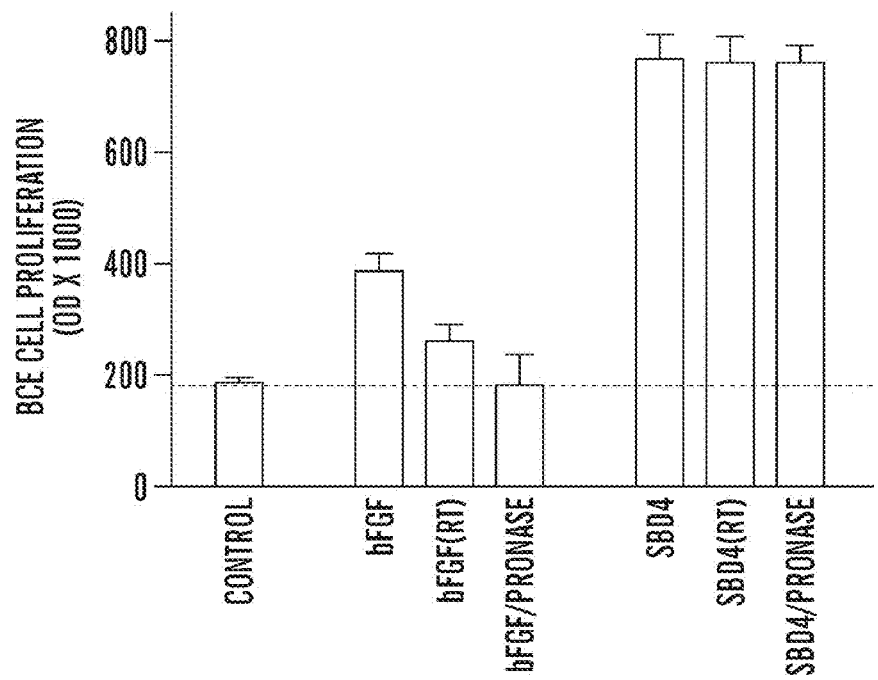

FIG. 2. Stimulatory effect of HPLC-purified SBD.4 on the proliferation of BCE (bovine capillary endothelial) cells, as compared with a potent angiogenesis stimulator bFGF, at different conditions. SBD.4 was tested on the proliferation of bovine capillary endothelial (BCE) cells in 96 well tissue culture plate, according to Skehan et coll. (1990). Cell number was estimated after 72 h of exposure to experimental treatments, and represented as optical density (OD) absorption of cell-associated sulforhodamine B staining at 570 nm. "(RT)" designates bFGF (1 ng/ml) or SBD.4 (2000 ng/ml) preincubated at room temperature for 7 days before activity test. "Pronase" signifies that the sample was preincubated with pronase (100 ug/ml in the presence of calcium) for 3 h at 37° C., before activity test. The dotted line indicates the baseline level of cell proliferation in the absence of any growth factors (Control). Error bars represent standard deviation. Number of tests (n)=3.

FIG. 3. Tridimensional tube formation assay, in vitro. A: Capillary endothelial cells form a monolayer in the absence of a remodeling stimulus. B: SBD.4 (5 µg/ml, purified by HPLC) induces remodeling of the monolayer that culminates in a tridimensional network of capillary structures. C: Remodeling response in the same model, induced by bFGF (10 ng/ml).

Figure 4A:
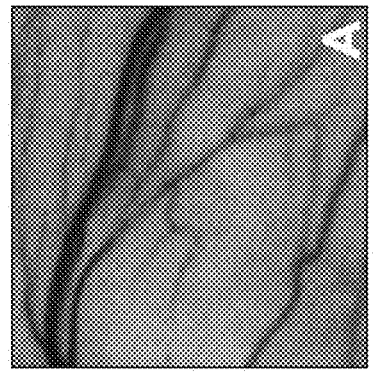
Figure 4B:
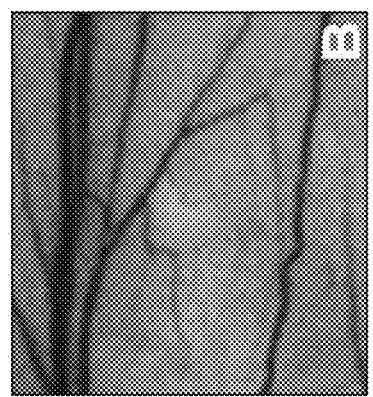
Figure 4C:
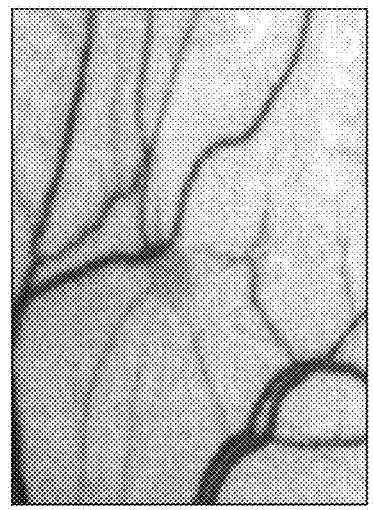

FIG. 4. Stimulation of angiogenesis by SBD.4 (50 micrograms/milliliter, 3 kD cut off filtration-purified) in the CAM assay (each panel is a reproduction of a color photograph). A: Avascular zone (in the middle of the panel), before putting the pellet. B: Same zone, 24 h later. Note a new blood vessel passing right through the pellet. C: A different experiment, showing a typical "spokes of a wheel" angiostimulatory effect 48 h after placement of the SBD.4 pellet.

Figure 5A:
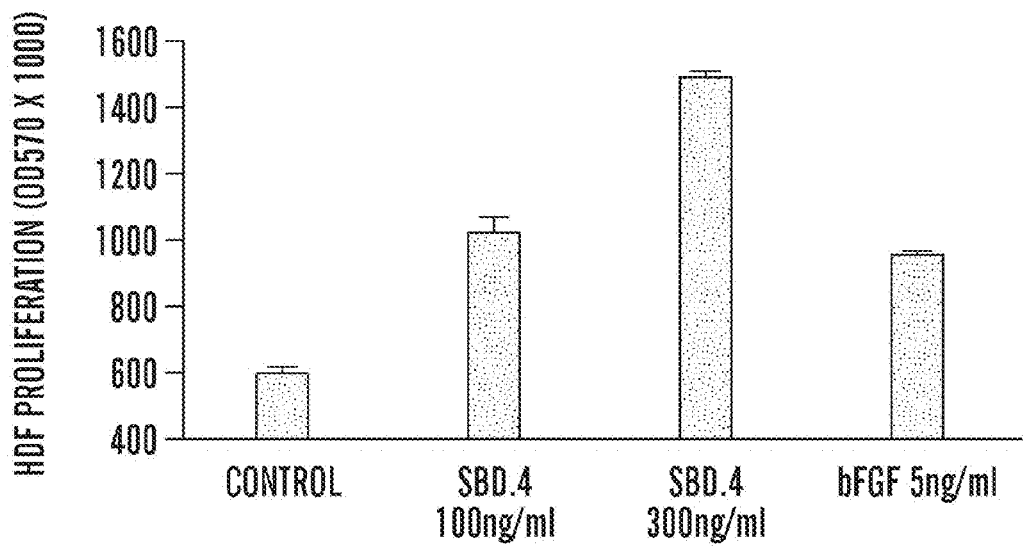

FIG. 5. Effect of SBD.4 (DEAE and HPLC-purified) on the proliferation of human dermal fibroblasts (HDF) and on the type I collagen in the medium conditioned by these cells. A: SBD.4 stimulates the proliferation of HDF. B: SBD.4 increases type I collagen levels in the HDF-conditioned medium, as measured by sandwich ELISA, according to Dobak and coll. (1994). Note that SBD.4 has stronger effect on collagen output and fibroblast proliferation than 5 ng/ml fibroblast growth factor (positive control). Error bars represent standard deviation. Number of tests (n)=3.

Figure 6:
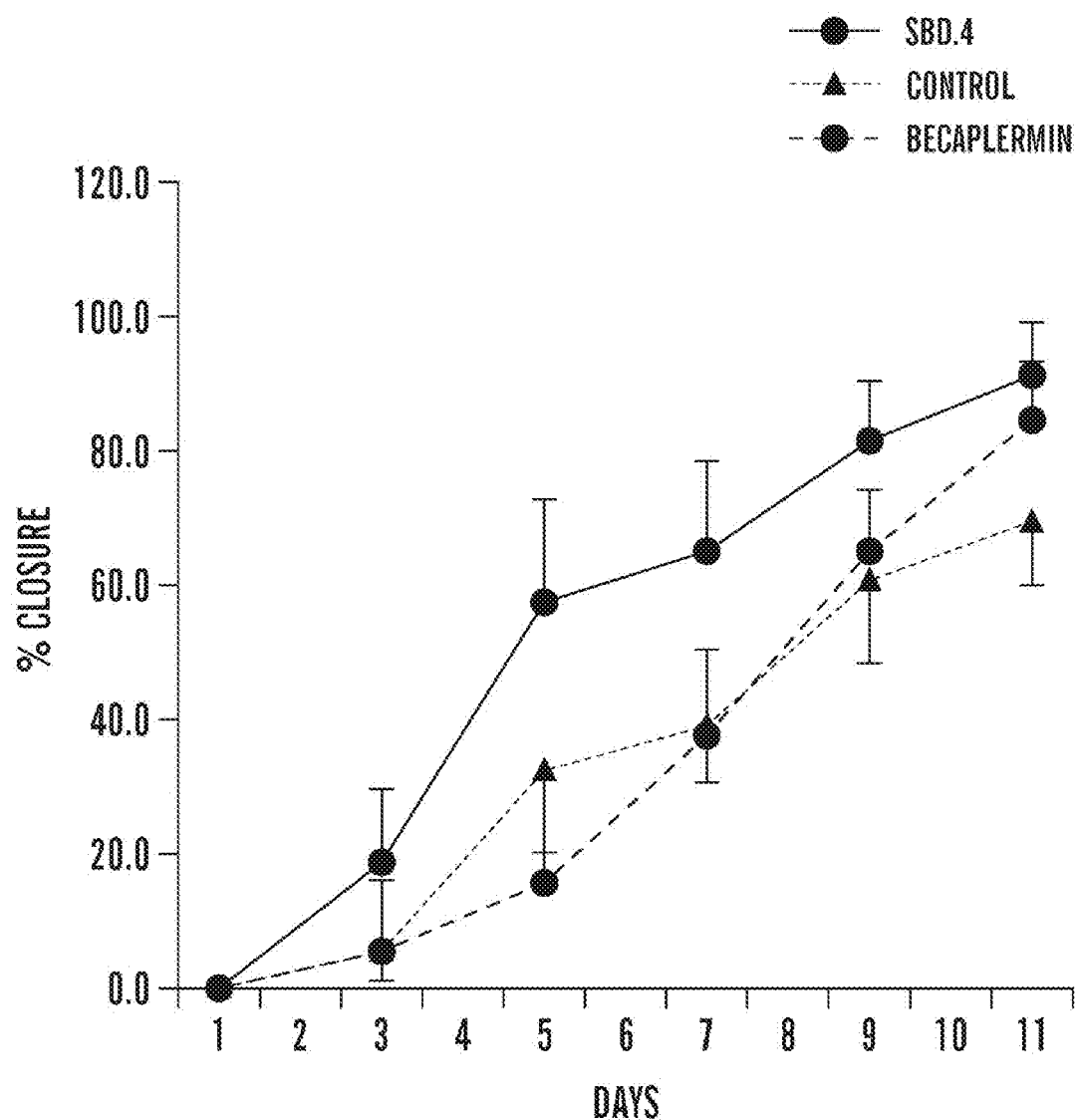

FIG. 6. Wound closure stimulated by SBD.4 (3 kd cut-off filtered aqueous extract) as compared with PBS (negative control) and becaplermin (positive control), in genetically diabetic mice. The stimulatory effect of SBD.4 was statistically significant while the effect of becaplermin was not meaningfully different from the control, as calculated by one-way analysis of variance (ANOVA). Each data point represents mean+/−SEM. n=12 for Control and n=6 for SBD.4 and becaplermin.

FIG. 7. Composition of SBD.4 at different levels of purification as defined by high pressure liquid chromatography-coupled mass spectrometry (HPLC-MS). Y axis represents the intensity of the signal, X axis represents elution time for panels A, C, D and mass-to-ion ratio (m/z)+1 (reflecting the molecular mass) for panels B, D, F. HP LC-MS conditions were: column flow: 0.5 ml/min; stoptime (run time): 10 min 30 sec; solvent conditions: Start: 95% solvent A (99.96% $H_2O$-0.04% formic acid)/5% solvent B (100% acetonitrile) Finish (at time 9 min): 90% solvent B/10% solvent A. The HPLC column was Reverse Phase C18 Synergy polar RP (Phenomenex, Torrance, Calif.) and the program was Polar-2 Agilent Easy Access Method. Further details are available on the panels. A-B: Composition SBD.4 purified by extracting the dry roots of *Angelica sinensis* (cut in pieces of approximately 0.5 cm×0.5 cm) in water at 25° C. for 20 min, filtered through 0.22 micron filter, then filtered through a 3 kilodalton (kD) cutoff centrifuge filter (Millipore). The three UV absorption profiles selected from the diode array spectrum of the SBD.4 eluate in panel A are (from top to bottom) at 254 nm (nanometer), 225 nm, 350 nm. The fourth panel represents the mass spectrometry (MS) profile of the HPLC eluate. The panel B represents a specific region of interest eluted from the column between 1.786 and 2.048 min. C-D: Composition of SBD.4 initially purified as mentioned in the description of panels A-B above, then further purified by one cycle of reverse phase C18 HPLC chromatography under the conditions described in the section "Methods of Preparation and Characterization of SBD.4". The three UV absorption profiles selected from the diode array spectrum of the SBD.4 eluate in panel C are (from top to bottom) at 254 nm, 225 nm, 350 nm. The fourth panel represents the MS profile of the HPLC eluate. MS analysis in panel D represents the region of interest eluted between 1.786 and 2.103 min. E-F: Composition of SBD.4 purified as mentioned in the description of panels A-B, then further purified by DEAE-cellulose (Pharmacia) chromatography as follows: one volume of SBD.4 solution was loaded on a DEAE-cellulose column of equivalent volume and the column was washed by 3 column volumes of $H_2O$, SBD.4 was eluted by 3 volumes of $NH_4OH$ pH 8 followed by 2 volumes of $H_2O$. The flow rate for a column of 2.5 cm diameter and 20 cm high was 2 ml/min throughout the whole DEAE-cellulose purification process. These 5 eluted volumes were pooled and lyophilized. The lyophilizate was dissolved in water in one fiftieth of the original volume of the pooled eluate, and methanol was added up to 75%. After homogenization, the solution was centrifuged and supernatant was collected, vacuum-dried, redissolved in water and purified on HPLC column, as detailed in the description of panels C-D. The four UV absorption profiles selected from the diode array spectrum of the SBD.4 eluate in panel E are (from top to bottom) at 225 nm, 254 nm, 350 nm and 280 nm. The fifth panel represents the MS profile of the HPLC eluate. The bottom graph on panel E represents ion extraction at 174 of the total ion current, showing the presence of a small amount of the 174D entity in this fraction. MS analysis in panel F represents the region of interest eluted between 1.749 and 1.861 min.

Figure 8:
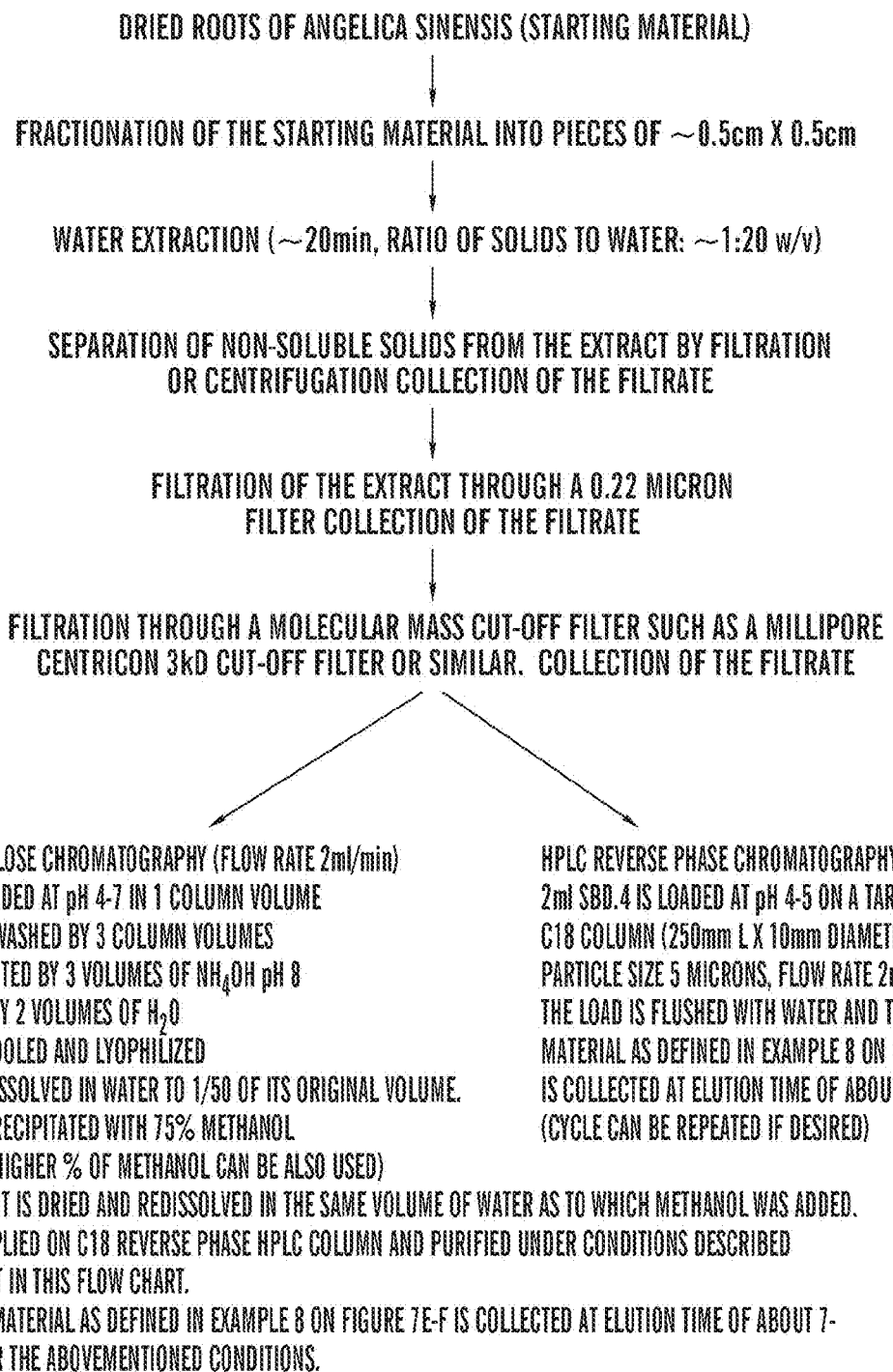

FIG. 8. Flow chart of *Angelica sinensis* component purification and characterization.

DETAILED DESCRIPTION OF THE INVENTION

Methods of Preparation and Characterization for SBD.4

The description here is to illustrate, not to limit, methods used to prepare SBD.4 (FIG. 8). First, SBD.4 is obtained by extracting the roots of *Angelica sinensis* in water, to provide the aqueous extract. Roots are placed in water at 5% (w:v) and brought to boil. The typical boiling time is 30 minutes and the typical extraction temperature is 98 degree Celsius. However, it is reasonable to assume that lower or higher ratio of roots: water, shorter or longer times of extraction as well as lower or higher temperature of extraction will result in the extraction of the same angiostimulatory material. For example, extraction at room temperature results in similar activity than extraction at higher temperatures. Also, it is reasonable to assume that the same SBD.4 angiostimulatory activity may be extracted with a solution combining water and alcohol including, but not limited to, methyl or ethyl alcohol, or another polar solvent.

Figure 7A:
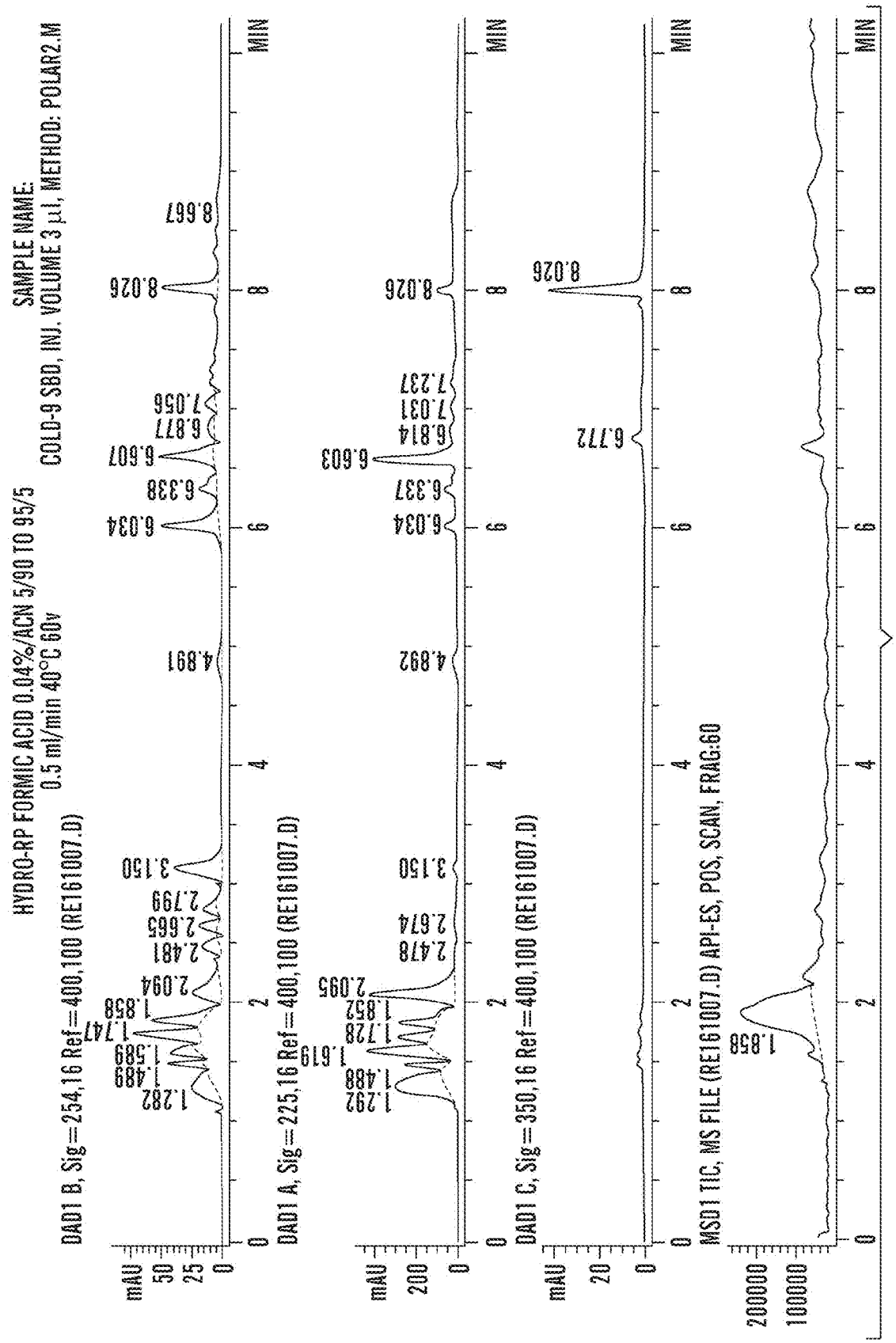
Figure 7B:
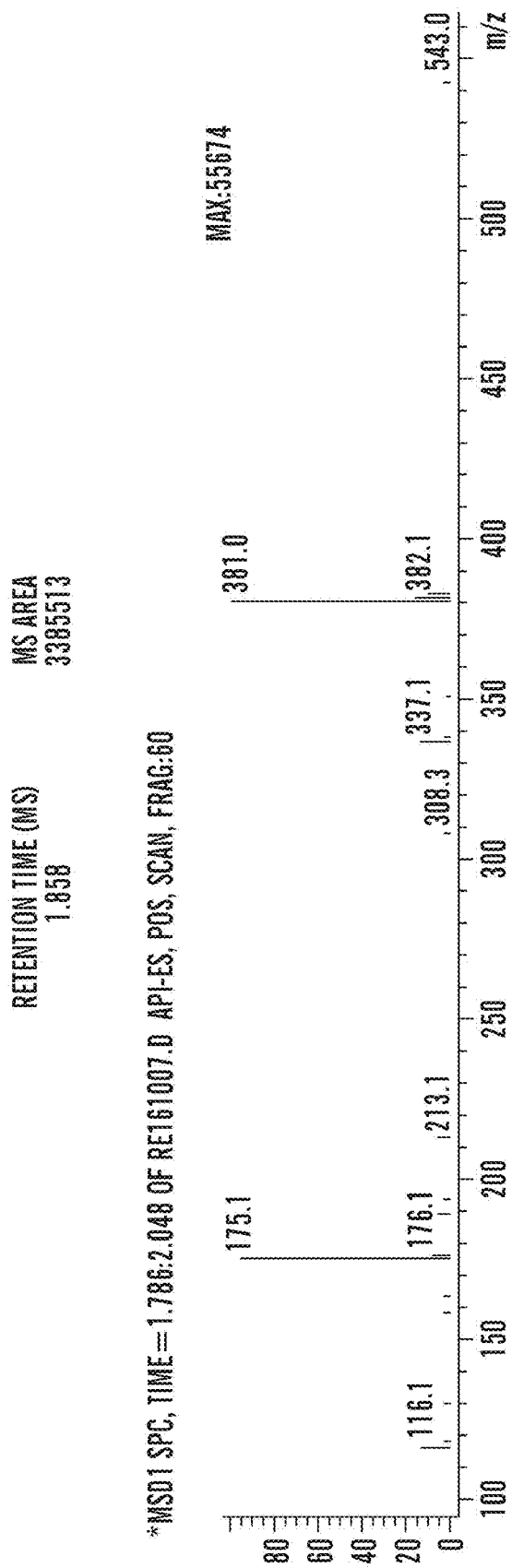
Figure 7C:
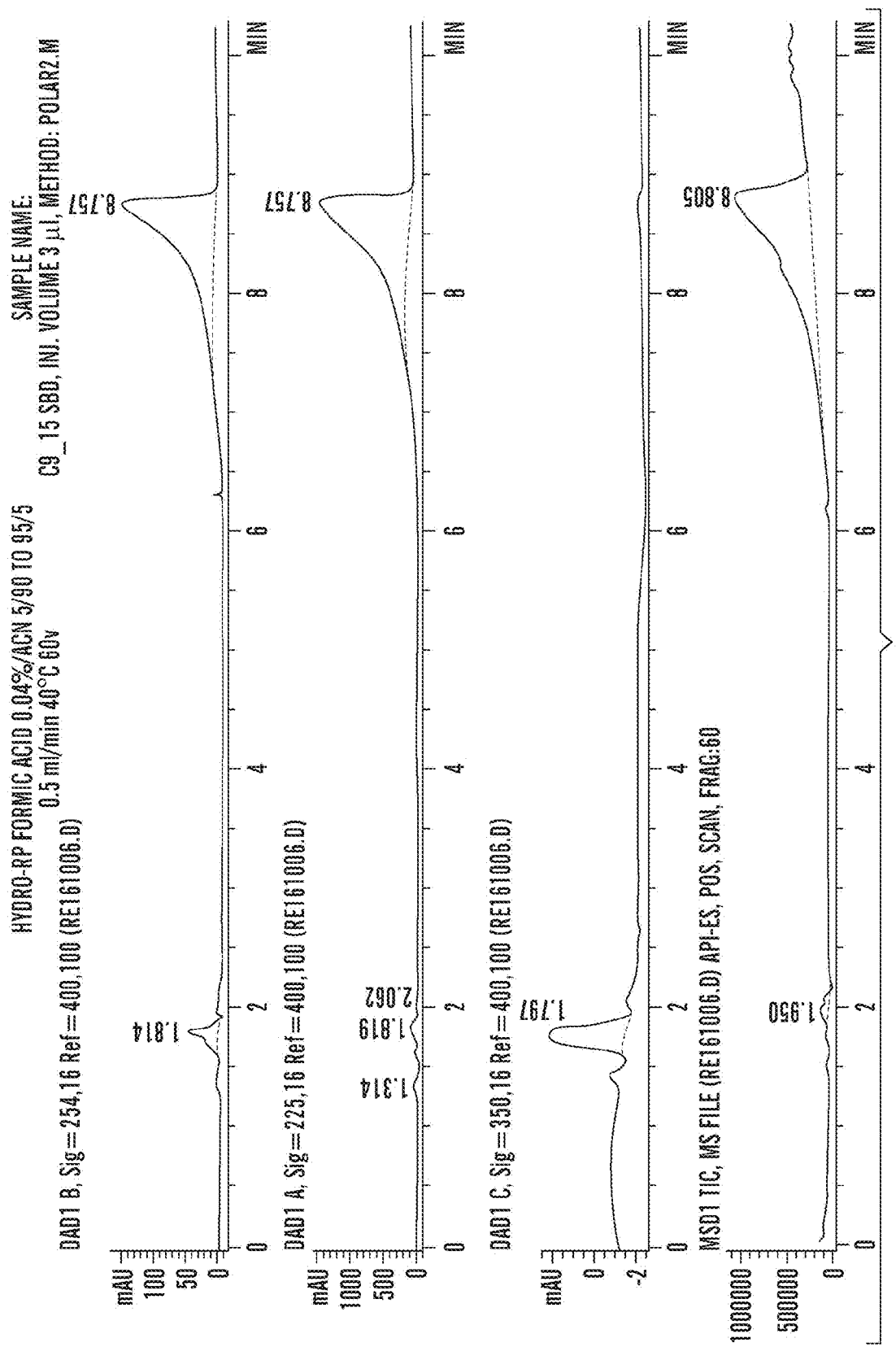
Figure 7D:
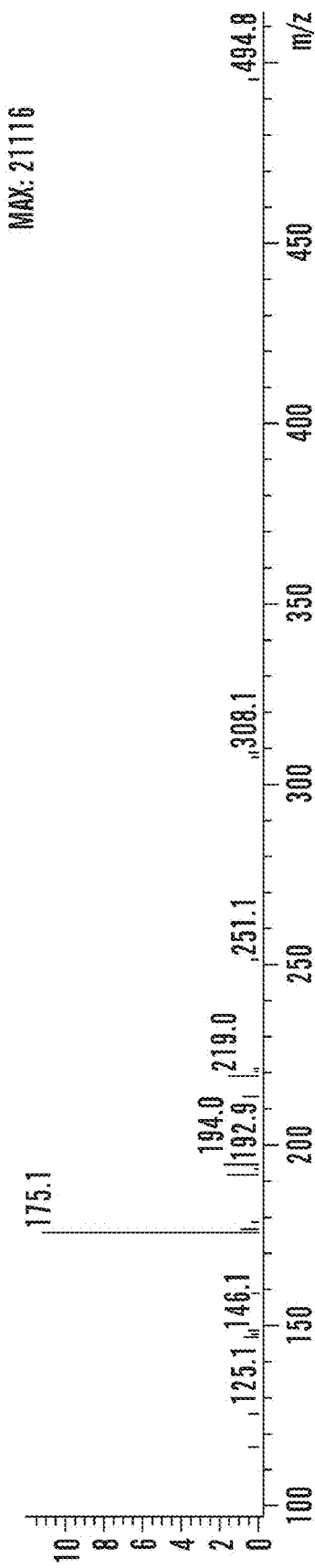

Following aqueous extraction, the extract mentioned above is centrifuged at the speed of about 2,000 g to remove insoluble particles, then sterile-filtered through a Nalgene (Rochester, N.Y.) 0.22 micron pore filter. Alternatively, the extract can be filtered through a set of filters of decreasing pore size, culminating with the filtration through 0.22 micron pore size filter. Pectinase can be added to the extract to improve its flow rate through filtering devices by digesting certain polysaccharides in the extract, without subsequent loss of biological activity of SBD.4. Furthermore, the aforementioned extract can be filtered through a centrifugal filter device of cut-off molecular weight of 10,000 daltons (Millipore, Bedford, Mass.) without loosing the activity mentioned in examples 1-7. The SBD.4 angiostimulatory material is collected in the lower chamber of the centrifugal filter device (Millipore. Bedford, Mass.), suggesting that the molecular weight of SBD.4 is less then 10,000 daltons (D). Furthermore, the extract can be filtered through a centrifugal device of three 3,000 D molecular weight cut-off (Millipore), and the angio- and fibroblast stimulatory material is collected in the lower chamber, suggesting that the molecular weight of this angiostimulatory material is 3,000 daltons or less. Such 3,000D cut off filter-purified SBD.4 has been used in Example 3, 5 and 6 (FIG. 6 and Tables I and II) and in Example 8 (FIG. 7A-B). Furthermore, the extract can be subjected to G10 Sepharose (Sigma, St. Luis) chromatography, which allows to separate compounds of molecular weight lower than 700 daltons from other components of the mix. When subjected to such chromatography, SBD.4 activity is absent fraction, which contains compounds of molecular weight higher than 700 daltons. On the contrary, SBD.4 is present in the third and fourth fraction (all fractions are of equal volume), which contains molecules of molecular weight lower than 700 daltons.

Figure 7E:
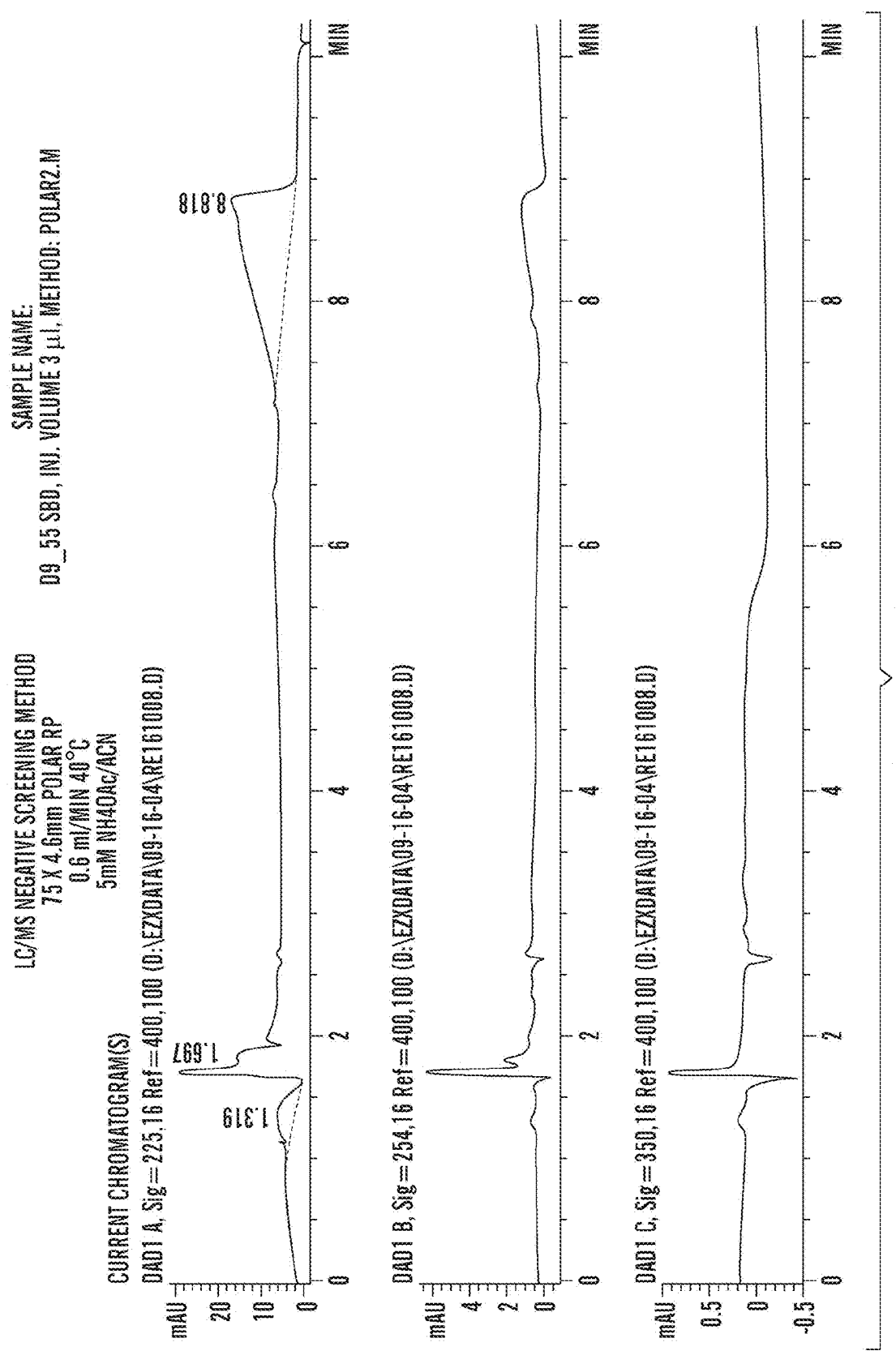
Figure 7E:
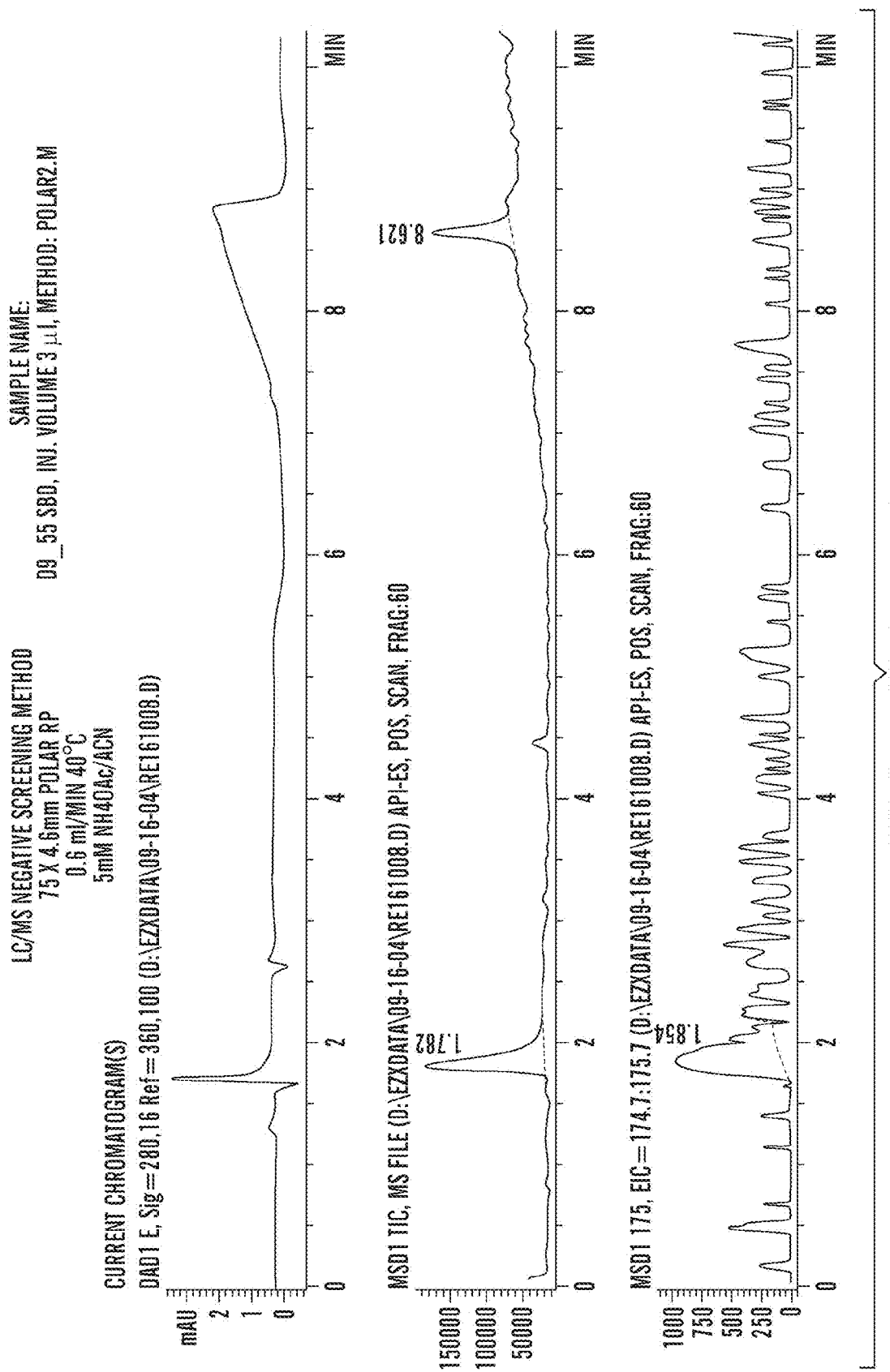
Figure 7F:
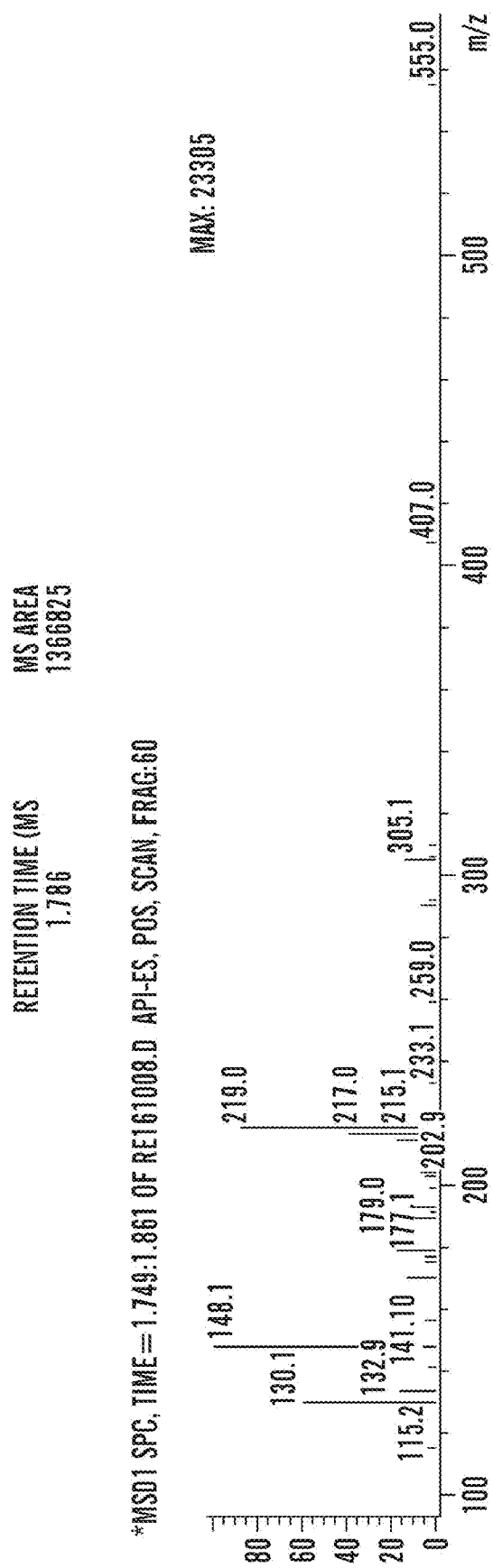

SBD.4 angiostimulatory material can be further purified by using the DEAE-cellulose chromatography (Pharmacia), whereas the cell stimulatory activity binds to DEAE-cellulose. Endothelial cell and fibroblast-stimulatory activity can be recovered from this resin by acid elution including, but not limited to 100 mM acetic acid and 100 mM hydrochloric acid, or weak alkaline elution such as $NH_4OH$ of pH about 8. Fibroblast-stimulatory activity can be recovered by the aforementioned conditions as well as by strong alkaline elution (100 mM NaOH). SBD.4 purified by loading on DEAE-cellulose, washing with water and eluting with $NH_4OH$ pH about 8, can be further purified by precipitation with 75% methanol, centrifugation, lyophilization of the supernatant, redissolution in water and purification by high pressure liquid chromatography (HPLC) on C18 reverse phase Targa (Higgins Analytical, Sunnyvale, Calif.) column. Lower or higher concentrations of methanol can be used instead of the above-mentioned 75%. The use of lower concentrations of methanol will result in the precipitation of fewer impurities, while at least a fraction of SBD.4 will remain in the supernatant precipitated with up to about 98% methanol. The active material (i.e. material, which stimulates endothelial and fibroblast cell proliferation) elutes relatively early (at ~7.5 min, sign ~ meaning "approximately" throughout this application) under the experimental conditions as follows: column dimensions: length: 250 mm; diameter: 10 mm; particle size: 5 microns. Sample is injected in 2 ml water, eluted in water (flow rate: 2 ml/min). Elution is monitored by refractometry and UV absorption at 245 nm. The HPLC-coupled mass spectrometry (HPLC-MS) analysis shows that one of the components in the active fraction is a molecular entity of 218 daltons. A smaller quantity of an entity of 174 daltons was also present (see Example 8, FIG. 7E-F). Such DEAF and HPLC-purified SBD.4 has been used in Example 4 (FIG. 5) and Example 8 (FIG. 7E-F).

In Example 2 (FIG. 2), Example 7 (Table III) and Example 8 (FIG. 7C-D) SBD.4 was purified as following: roots of *Angelica sinensis* are water-extracted and filtered through 0.22 micron filter, as described above. The extract was then filtrated through a 5000 daltons molecular cut-off Pellicon XL 50 Biomax filter (Millipore) and subjected to HPLC chromatography on reverse phase C18 Targa (Higgins Analytical, Sunnyvale, Calif.) column. The active material (i.e. material, which stimulates endothelial and fibroblast cell proliferation) eluted relatively early (at ~7.5 min). The experimental conditions were as Sample was injected in 2 ml water, eluted in water (flow rate: 2 ml/min). Elution was monitored by refractometry and UV absorption at 245 nm.

Furthermore, SBD.4 can be also purified by aforementioned water extraction and filtration, followed by sequential methanol precipitation and high pressure liquid chromatography (HPLC) on C18 reverse phase column, as described below: Roots of *Angelica sinensis* were water-extracted and filtered through 0.22 micron filter, as described above. The extract was then filtrated through a 5000 daltons molecular cut-off Pellicon XL 50 Biomax filter (Millipore). The filtrate (12 g solid solubilized in 400 ml water) was collected and concentrated under vacuum in a rotovap to about 25 ml. Three hundred ml of methanol were added, stirred overnight and precipitated solids (Fraction 1, about 3.7 g) were separated from the supernatant by centrifugation. The supernatant was dried in rotovap, 3.2 g of the dried material was dissolved in 18 ml of water and 3 ml of methanol were added. The resulting precipitate (Fraction 2) was separated from the supernatant, the supernatant was evaporated, dissolved in 9 ml of water and 3 ml of methanol were added. The resulting precipitate (Fraction 3) was separated by centrifugation and the supernatant was dried and redissolved in 3 ml water, to which 3 ml of methanol were added. After removing the precipitated material, the supernatant was dried and its weight was estimated at 1.2 g (Fraction 4). The bioactivity of the fractions 1-4 was compared (by measuring its endothelial cell stimulatory activity, as in example 1), and Fraction 4 was found to be the most active. SBD.4 can be lyophilized and redissolved in water without loosing the aforementioned endothelial and fibroblast cell stimulatory activity.

SBD.4 is an aqueous extract from roots of Chinese medicinal herb *Angelica sinensis*. Preferably, SBD.4 is a molecule or an extract of molecules of molecular weight of ten thousand daltons or less. More preferably, it is a molecule or an extract of molecules of molecular weight of three thousand daltons or less. Most preferably, it is a molecule or an extract of molecules of 700 daltons or less.

SBD.4 is heat-stable. Angiostimulatory activity of SBD.4 is maintained even after boiling for 30 minutes in water at ninety five degrees centigrade.

SBD.4 binds to diethylaminoethyl cellulose (DEAE) cellulose ion-exchange resin and to reverse-phase resins, and is recovered by selected elution buffers.

SBD.4 is stable at pH 7. More preferably, SBD.4 is stable at a pH range of at least 3-8

SBD.4 can be acetylated with the use of pyridine and acetic anhydride (a method useful for acetylation of sugars and aminoacids), which indicates the presence of hydroxyl of SBD.4 can be reversed only partially, it is assumed that both amino group(s) and hydroxy group(s) are present in SBD.4.

SBD.4 is very polar, because it elutes relatively early (at ~7.5 min) from Targa C18 HPLC reverse phase column. Column dimensions are: length: 250 mm; diameter: 10 mm; particle size: 5 microns. Sample is injected in 2 ml water, eluted in water (flow rate: 2 ml/min). SBD.4 may be administered to humans in various forms such as tablets, hard gelatin capsules, or liquid preparations, as oral medicines, wound dressings, topical drugs or skin care products, or injectable drugs.

The above-described methods are useful in obtaining active components from *Angelica sinensis* for the following application. However, the description is not meant to restrict the use in *Angelica sinensis* species only, the genus *Angelica* including but not limited to European and American *Angelica* species, or sometimes the family Umbelliferae is within the scope of the present invention.

Pharmaceutical Applications

The present invention provides a pharmaceutically acceptable formulation of SBD.4—a water extract (also referred hereto as crude aqueous extract) from the roots of *Angelica sinensis*, a fraction or a lyophilizate thereof, or one or more active components contained in said extract, useful in the methods of the present invention. In one embodiment, SBD.4 is packaged in a sachet that is decanted into a potable liquid for oral administration to the patient. In this embodiment, the liquid can be a syrup or, more conveniently, a commonly consumed liquid, such as water, fruit juice, or cola. In another embodiment, the *Angelica sinensis* extract is formulated as a tablet or pill. In yet another embodiment, SBD.4 is formulated in a medical device, such as, but not limited to a wound dressing. A decided practical advantage of the compounds of the present invention is that the compounds can be administered in any convenient manner such as by the oral, intravenous, intramuscular, topical, or subcutaneous routes.

Thus, *Angelica sinensis* extracts can be orally administered, for example, with an inert diluent or with an assimilable edible carrier, including, but not limited to a power bar, or it can be enclosed in hard or soft shell gelatin capsules, or compressed into tablets, or incorporated directly with the food of the diet. For oral therapeutic administration, *Angelica sinensis* extracts can be incorporated with excipients and used in the form of ingestible tablets, buccal tablets, troches, capsules, elixirs, suspensions, syrups, wafers, and the like. therapeutically active doses described above. In some embodiments, the formulation will be glucose-free.

The tablets, troches, pills, capsules, and the like may also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as saccharin; and/or a flavoring agent such as peppermint, oil of wintergreen, or cherry flavoring. When the dosage unit form is a capsule, it can contain, in addition to materials of the above types, a liquid carrier. Various other materials can be present as coatings or to otherwise modify the physical form of the dosage unit. For instance, tablets, pills, or capsules can be coated with shellac. A syrup or elixir can contain the active compound, a sweetening agent, methyl and propylparabens as preservatives, and a flavoring such as cherry or orange flavor. Of course, any material used in preparing any dosage unit form should be pharmaceutically pure and substantially non-toxic in the amounts employed. In addition, the active compound can be incorporated into sustained-release preparations and formulations. The *Angelica sinensis* extract can also be administered parenterally or intraperitoneally. A solution of the active compound as a free acid or pharmacologically acceptable salt can be prepared in water suitably mixed with a surfactant such as hydroxypropylcellulose. Dispersions can also be prepared in glycerol, liquid polyethylene glycols and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and, in final form, must be fluid to the extent that easy syringability exists. It must be preserved against the contaminating action of microorganisms such as bacteria and fungi.

The pharmaceutical forms suitable for topical use include oil and water emulsions and liposomal formulations, as well as lotions, creams, carriers and ointments commonly used for topical administration of drugs, including, but not limited to carboxymethylcellulose, poly-lactic/glycolic acid, hydroxypropyl/methylcellulose, carboxymethylcellulose foam, hydroxyapatite or hyalouronic gel.

SBD.4 may be also useful for the treatment of wounded, damaged or otherwise fragilized skin, like the diabetic skin under the form of aqueous soaking solution.

The carrier can be a solvent or dispersion medium containing, for example, water, ethanol, polyol, for example, glycerol, propylene glycol, and liquid polyethylene glycol, and the like, suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonic agents, for example sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filtered sterilization. Generally, dispersions are, prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile filtered solution thereof.

As used herein, a "pharmaceutically acceptable carrier includes any and all solvents, dispersion media, coatings, antibacterial and antifungal agents, isotonic agents, absorption delaying agents, and the like. The use of such media and agents for pharmaceutical active substances is well known in the art. Except insofar as any conventional media or agent is incompatible with the active ingredient, its use in the therapeutic compositions of the invention is contemplated. Supplementary active ingredients can be incorporated into the compositions of the invention.

It is essentially advantageous to formulate parental and other compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier.

Another aspect of the invention includes but is not limited to, promoting angiogenesis in tissue by directly contacting the tissue with SBD.4 in an amount effective to promote angiogenesis in said tissue. One embodiment of the invention is promoting angiogenesis in a tissue selected from the group consisting of endothelial, cardiac, cerebral, muscular, vascular, transplanted, dermal, epidermal or wounded. Another embodiment is that the tissue could also be ischemic wherein the ischemic tissue is selected from the consisting of myocardial ischemic tissue, cerebral ischemic tissue, veno-occlusive diseased tissue, wounded tissue, damaged dermal tissue, damaged epidermal tissue, diabetic tissue and myocardial ischemic tissue wherein said myocardial ischemic tissue is implicated in coronary artery diseases.

The stimulation of angiogenesis and fibroblast growth by SBD.4 from herb extract of *Angelica sinensis* may be a valuable treatment for ischemic diseases, such as, but not limited to cardiovascular and peripheral ischemic diseases, stroke, peptic ulcers, wounds, diabetic skin and other diabetic tissues, for bone regeneration, for personal care (such as skin, lip, hair care), and for other conditions where the stimulation of fibroblast growth and angiogenesis, or protection of vascular networks is beneficial.

The pharmaceutical formulation methods described above can be similarly applied to the following wound-healing application.

Wound-Healing Applications

The present invention provides improved methods for promoting wound healing and reducing scar formation. In particular, an aqueous extract from the roots of *Angelica sinensis* or a fraction or a lyophilizate thereof, or one or more active components contained in said extract, provide significant improvements over the prior art method of promoting wound or reducing scar formation.

As used herein, the term "wound" is used throughout the specification to describe skin wounds, which are treated by the formulations and the methods, described herein as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. The compositions and methods of the invention are useful for enhancing the healing of all wounds of the skin. In particular, the present invention provides methods and compositions suitable for treatment of wounds in diabetics, normal patients and A "tissue wound" as used herein is a wound to an internal organ, such as a blood vessel, intestine, colon, etc. The materials of the invention are useful for enhancing the wound healing process in tissue wounds whether they arise naturally or as the result of surgery. For instance, during the repair of arteries the vessel needs to be sealed and wound healing must be promoted as quickly as possible. The compositions of the invention can speed up that process. The compositions of the invention are also particularly useful for the treatment of damaged tissues in the digestive system.

The methods of the invention are also useful for preventing scar formation. The compositions can be used to prevent the formation of a scar at the same time as promoting wound healing. Alternatively, the compositions may be used for preventing scar formation by reducing or initiating regression of existing scars. Scar tissue as used herein refers to the fiber rich formations arising from the union of opposing surfaces of a wound.

The compositions and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetyl pyridinium chloride, antibiotics, and analgesics.

Growth factors include, but are not limited to, fibroblast growth factors (FGF), FGF-1, FGF-2, FGF-4, thymosins, platelet-derived growth factors (PDGF), insulin-binding growth factors (IGF), IGF-1, IGF-2, epidermal growth factor (EGF), transforming growth factor (TGF), TGF-.alpha., TGF-.beta., cartilage inducing factors-A and -B, osteoid-inducing factors, osteogenin, bone morphogenic proteins, and other bone growth factors, collagen growth factors, heparin-binding growth factor-1 or -2, and their biologically active derivatives. The compositions may also include antiseptics.

Cosmetic Applications

An aqueous extract from *Angelica sinensis* or a fraction or a lyophilizate thereof, or one or more active components contained in said extract, may be utilized in the formulation of cosmetic compositions because of its novel properties in not only protecting and enhancing microcirculation and dermal fibroblast growth, but also stimulating collagen I levels and fibroblasts.

Cosmetic compositions are preparations applied to the surface of the body for the purpose of enhancing its appearance. These compositions can be make-up preparations, the body surface, or treatment preparations, which effect no immediately noticeable change but which, after repeated use, are expected to have a beautifying effect.

The cosmetic compositions of the present invention may be skin care products such as lotions, creams, shampoos, cleansers, make-up foundations, footbaths, etc. The compositions of the invention may be emulsions of liquid or semi-liquid consistency of the milk type, obtained by dispersion of an oil phase in an aqueous phase or vice versa; or suspensions or emulsions of soft consistency of the cream type.

All oils used in the production of cosmetic compositions are suited for use in the compositions of the present invention. There may be mentioned hydrocarbons such as mineral oils, petrolatum and squalane; animal and vegetable triglycerides such as almond oil, peanut oil, wheat germ oil, linseed oil, jojoba oil, oil of apricot pits, oil of walnut, oil of palm nuts, oil of pistachio nuts, oil of sesame seeds, oil of rapeseed, cade oil, corn oil, peach pit oil, poppyseed oil, pine oil, borage oil, castor oil, soybean oil, *Lycium barbarum* oil, avocado oil, safflower oil, coconut oil, hazelnut oil, olive oil, grapeseed oil, and sunflower seed oil; hydroxy-substituted $C_8$-$C_{50}$ unsaturated fatty acids and esters thereof, $C_1$-$C_{24}$ esters of $C_8$-$C_{30}$ saturated fatty acids such as isopropyl myristate, cetyl palmitate and octyldodecylmyristate (Wickenol 142); beeswax; saturated and unsaturated fatty alcohols such as behenyl alcohol and cetyl alcohol; fatty sorbitan esters; lanolin and lanolin derivatives; $C_1$-$C_{24}$ esters of dimer and trimer acids such as diisopropyl dimerate, diisostearylmalate, diisostearyldimerate and triisostearyltrimerate; and silicones such as water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof.

It is possible to use standard antioxidants such as t-butyl hydroquinone, butylated hydroxytoluene and .alpha.-tocopherol and its derivatives, alpha lipoic acid, resveratrol and its derivatives in the cosmetic compositions of the present invention, preferably, in amounts less than would normally be utilized.

Similarly, it is possible to use standard preservatives such as methyl, ethyl, propyl, butyl and isobutyl p-hydroxybenzoate (parabens), 2-phenoxyethanol, sorbic acid, potassium sorbate, hexamidine diisothionate, imidazolidinylurea (Germall 115) or preservatives marketed under the names Kathon and Tridssan.

A wide variety of optional ingredients such as non-occlusive moisturizers, humectants, gelling agents, neutralizing agents, perfumes, coloring agents and surfactants can be added to the presently contemplated cosmetic compositions.

A humectant may be present in an amount of from about 0.1% to about 20%, preferably from about 1% to about 10% and especially from about 2% to about 5% by weight of the total composition. Suitable humectants include sorbitol, propylene glycol, butylene glycol, hexylene glycol, ethoxylated glucose derivatives, hexanetriol, glycerin, water-soluble polyglycerylmethacrylate lubricants (e.g., compositions available under the trademark Lubrajel) and panthenols (e.g. D-panthenol).

A hydrophilic gelling agent may be present in an amount of from about 0.01% to about 10%, preferably from about 0.02% to about 2% and especially from about 0.02% to about 0.5% by weight of the total composition. Suitable hydrophilic gelling agents include cellulose ethers (e.g., hydroxyethyl cellulose, hydroxypropylmethyl cellulose), polyvinylalcohol, guar gum, hydroxypropyl guar gum and xantham gum, as well as the acrylic acid/ethyl acrylate copolymers and the carboxyvinyl polymers sold under the trademark Carbopol.

Neutralizing agents, suitable for use in neutralizing acidic group containing hydrophilic gelling agents, include sodium hydroxide, potassium hydroxide, ammonium hydroxide, monoethanolamine, diethanolamine and triethanolamine.

Other optional materials include keratolytic agents such as salicylic acid; proteins and polypeptides and derivatives thereof; soluble or colloidally-soluble moisturizing agents such as hylaronic acid and starch-grafted sodium polyacrylates; coloring agents; perfumes and perfume solubilizers; surfactants/emulsifiers such as fatty alcohol ethoxylates and ethoxylated polyol fatty acid esters; and pigments which can be organic or inorganic and which include materials having a low color or lustre, such as matte finishing agents, and also light scattering agents.

Incorporation of a UV protective agent into the preparation of the present invention makes it possible to suppress undesired actions of UV light that would otherwise undermine microcirculation and dermal fibroblast growth.

The UV screening agent which can be used in the present invention is not particularly limited as long as it can be incorporated physicochemically into the preparation of the present invention and is capable of producing the above-described synergistic effects when incorporated into the preparation. Examples of suitable UV protective agents are shown UV-A absorbers include anthranilic acid derivatives, such as methyl anthranilate and homomentyl N-acetylanthranilate; benzophenone derivatives, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salts, 4-phenylbenzophenone, 2-ethylhexyl-4'-phenylbenzophenone-2-carboxylates, 2-hydroxy-4-n-octoxybenzophenone, and 4-hydroxy-3-carboxybenzophenone; benzotriazole derivatives, such as 2,2'-hydroxy-5-methylphenylbenzotriazole, 2-(2'-hydroxy-5'-t-octylphenyl)benzotriazole and 2-(2'-hydroxy-5'-methylphenyl)benzotriazole; dianisoylmethane, and 4-methoxy-4'-t-butyldibenzoylmethane (Parsol A™). Preferred of these UV-A absorbers are 4-methoxy-4'-t-butyldibenzoylmethane, 2-hydroxy-4-methoxybenzophenone, and 2-hydroxy-4-methoxybenzophenone derivatives, e.g., 2-hydroxy-4-methoxybenzophenone-5-sulfonic acid salts, for their safety and efficacy.

Medium-wavelength ultraviolet (hereinafter referred to as UV-B) absorbers include benzoic acid derivatives, such as p-aminobenzoic acid (hereinafter abbreviated as PABA), glycerol mono-PABA ester, N,N-dipropoxyPABA ethyl ester, N,N-diethoxyPABA ethyl ester, N,N-dimethylPABA ethyl ester, N,N-dimethylPABA butyl ester, and N,N-dimethylPABA amyl ester, salicylic acid derivatives, such as dipropylene glycol salicylate, ethylene glycol salicylate, myristyl salicylate, methyl salicylate, amyl salicylate, mentyl salicylate, homomentyl salicylate, octyl salicylate, phenyl salicylate, benzyl salicylate, and p-isopropylphenyl salicylate; cinnamic acid derivatives, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl .alpha.-cyano-.beta.-phenylcinnamate, 2-ethylhexyl .alpha.-cyano-.beta.-phenylcinnamate, glycerol mono-2-ethylhexanoyl-di-p-methoxycinnamate, octyl methoxycinnamate, 3-methyl-4-ethylbis(trimethylsiloxy)silyl-!butyl 3,4,5-trimethoxycinnamate, and monoethyl p-dimethoxycinnamate; camphor derivatives, such as 3-(4'-methylbenzylidene)-d, 1-camphor, 3-benzylidene-d,1-camphor, and 5-(3,3-dimethyl-2-norbornylidene)-3-pentene-2-one; urocanic acid, ethyl urocanate, 2-phenyl-5-methylbenzoxazole, and dibenzalazine.

The UV screening agents include titanium oxide (TiO$_2$), talc (MgSiO$_2$), Carmine (FeO$_2$), bentonite, kaolin, and zinc oxide (ZnO).

These UV protective agents can be incorporated into the preparation of the present invention in an appropriate combination thereof in agreement with the particular purpose and form of the preparation. Collagen cross-linking is a phenomenon which occurs mainly in the dermal layer of the skin. Where a UV protective agent is used for the specific purpose of affecting synergistic inhibitory action on collagen cross-linking, it is recommended to select UV-A absorbers which absorb UV-A (wavelength: 320 to 400 nm) capable of reaching the dermal layer rather than UV-B absorbers which absorb UV-B (wavelength: 280 to 320 nm). It is particularly preferred in the present invention to positively use UV-A absorbers for the purpose of producing synergistic inhibitory effects on collagen cross-linking.

The denotation "UV-A absorbers" or "UV-B absorbers" as used herein does not always mean that the agents are capable of absorbing only UV-A or UV-B but means that they are capable of absorbing at least UV-A or UV-B. For example, the benzophenone UV absorbers mentioned above as examples of UV-A absorbers are capable of absorbing UV-B as well as UV-A.

The amount of the UV protective agent to be incorporated is subject to variation depending on the properties to be imparted to the preparation of the present invention. It is usually 0.01 to 30% by weight, preferably 0.1 to 20% by weight, based on the total preparation. If the amount is less than 0.01% by weight, the agent tends to fail to bring about synergistic effects that would have been obtained by addition of a sufficient amount of the agent. If the amount exceeds 30% by weight, any further enhancement of synergistic effects that might be expected from employing the increased amount hardly results.

The inclusion of a whitening effect in the preparation is effective for alleviating the bad influences of UV light on the skin. To this effect, a whitening agent, such as placental extract, glutathione, extract of creeping saxifrage (*Saxifraga stolonifera*), etc. may be added to the preparation.

The provision of an anti-inflammatory effect in the preparation is effective for alleviating the bad influences of UV light on the skin. To this effect, an anti-inflammatory agent, such as a glycyrrhizic acid derivative, a glycyrrhetic acid derivative, a salicylic acid derivative, hinokitiol, zinc oxide, etc. may be added to the preparation.

Over-the-Counter/Food and Drug Administration-approved skin soothing agents, such as, but not limited to dimethicone and allantoin can be added to the preparation of the It is also possible to add various plant extracts into the preparation for various purposes. Examples of usable plant extracts are phellodendron extract, coptis roots extract,

*Lithospenni radix* extract, *Paeoniae radix* extract, *Lycium barbarum* extract, *Swertia* extract, birch extract, *Rhodiola* extract, olive leaf extract, grapeseed extract, *Arnica* extract, sage extract, loquart extract, ginseng extract, aloe extract, common mallow extract, iris extract, grape extract, Coicis semen (*Coix lachryma-jobi*) extract (Yokuinin), loofah (*Luffa cylindrica* Rosem) extract, Lilium extract, crocus extract, *Cnidii rhizoma* extract, ginger extract, Saint-John's wort (*Hypericum erectum*) extract, petty white (*Ononis spinosa*) root extract, rosemary extract, garlic extract, capsicum extract, and orange peel.

Vitamins may also be added to the preparation in order to impart various peculiar effects to the preparation, for example, a cutaneous aging inhibitory effect. Examples of usable vitamins are vitamin A's, such as vitamin A oil, retinol, retinol acetate; vitamin $B_1$; vitamin $B_2$'s, such as riboflavin, riboflavin butyrate, and flavin adenine dinucleotide; $B_3$; vitamin $B_5$; vitamin $B_6$'s, such as pyridoxine hydrochloride and pyridoxine dioctanoate; vitamin $B_{12}$; vitamin C's, such as L-ascorbic acid, L-ascorbic acid palmitate, L-ascorbic acid 2-sulfate, L-ascorbic acid phosphate, and DL-α-tocopherol-L-ascorbic acid phosphate diester dipotassium; pantothenic acid derivatives, such as calcium pantothenate, D-pantothenyl alcohol, pantothenyl ethyl ether, and acetylpentothenyl ethyl ether, vitamin D's, such as ergocalciferol and cholecalciferol; nicotinic acid compounds, such as nicotinic acid, nicotinamide, and benzyl nicotinate; vitamin E's, such as α-tocopherol, tocopherol acetate, DL-α-tocopherol nicotinate, and DL-α-tocopherol succinate; and other vitamins such as vitamin P; folate and biotin.

Minerals may also be added to the preparation in order to impart microelements required for the optimal skin metabolism, such as magnesium, zinc and copper, under various forms such as, but not limited to magnesium aspartate, zinc gluconate or copper gluconate.

Other active ingredients, which may be incorporated into the preparation of the present invention include peptides, amino acids, polysaccharides and peptidoglycans.

The active ingredients which may be incorporated into the preparation of the present invention are not limited to the above-enumerated specific examples. Further, the pharmacological efficacy of the above-enumerated active ingredients is not limited to the one described. For example, vitamin C's are useful as not only a whitening agent but also an antioxidation assistant. These active ingredients may be incorporated into the preparation either individually or as an appropriate combination of two or more thereof according to the The present invention is broadly applicable to cosmetics, pharmaceuticals and non-medical applications which are externally applied to the skin and may take a wide variety of forms, such as aqueous solutions, solubilized systems, emulsions, powders, oily liquids, gels, ointments, aerosols, water-oil two phase systems, water-oil-powder three phase systems, and the like. For example, the preparations of the present invention are applicable to a wide range of cosmetic forms, such as facial cleansers, clear lotions, milky lotions, creams, jellies, skin revitalizers, and facial packs as skin care cosmetics, and foundation creams as makeup cosmetics; and a wide range of pharmaceutical or non-medical application forms, such as ointments. The forms applicable to the preparations of the present invention are by no means limited to the above-mentioned specific dose forms.

The preparations according to the present invention may comprise a wide variety of known bases or vehicles according to the desired dose form as long as the effects of the present invention are not impaired. Such bases or vehicles include oils, e.g., avocado oil, tubaki oil (camellia oil), evening primrose oil, Turtle oil, Macadamia nut oil, corn oil, mink oil, olive oil, rape oil, egg yolk oil, sesame oil, persic oil (apricot kernel oil), wheat germ oil, sasanqua oil, castor oil, linseed oil, safflower oil, cotton seed oil, perilla oil, soybean oil, peanut oil, tea seed oil, kaya (*Torreya nucifera*) oil, rice bran oil, Chinese tung oil, Japanese tung oil, jojoba oil, germ oil, triglycerides (e.g., glycerol trioctanoate and glycerol triisopalmitate); fats, such as cacao fat, coconut oil, horse fat, hardened coconut oil, palm oil, beef tallow, mutton tallow, hardened beef tallow, palm kernel oil, lard, beef bone fat, haze (*Rhus succedancea* L.) kernel oil, hardened oil, beef foot oil, Japan wax, and hardened castor oil; waxes, such as molasses, candelilla wax, cotton wax, carnauba wax, bayberry wax, cera ibota, whale wax, montan wax, rice bran wax, lanolin, kapok wax, lanolin acetate, liquid lanolin, sugar cane wax, lanolin fatty acid isopropyl ester, hexyl laurate, hydrogenated lanolin, jojoba wax, hard lanolin, Shellac wax, polyoxyethylene (hereinafter abbreviated as POE) lanolin alcohol ether, POE lanolin alcohol acetate, POE cholesterol ether, polyethylene glycol lanolin fatty acid ester, and POE hydrogenated lanolin alcohol ether, hydrocarbon oils, such as liquid paraffin, ozokerite, squalene, pristane, paraffin, ceresin, vaseline, and microcrystalline wax; higher fatty acids, e.g., lauric acid, myristic acid, palmitic acid, stearic acid, behenic acid, oleic acid, 12-hydroxystearic acid, undecylenic acid, Tall oil, isostearic acid, linoleic acid, linolenic acid, eicosapentaenoic acid (EPA), and docosahexaenoic acid (DHA); higher alcohols including straight-chain alcohols, such as lauryl alcohol, cetyl alcohol, stearyl alcohol, behenyl alcohol, myristyl alcohol, Oleyl alcohol, and cetostearyl decyltetradecinol, lanolin alcohol, cholesterol, phytosterol, hexyldodecanol, isostearyl alcohol, and octyldodecanol; synthetic ester oils, such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, diisostearyl malate, glycerol di-2-heptylundecanoate, trimethylolpropane tri-2-ethylhexylate, trimethylolpropane triisostearate, pentaerythritol tetra-2-ethylhexylate, glycerol tri-2-ethylhexylate, trimethylolpropane triisostearate, cetyl 2-ethylhexylate, 2-ethylhexyl palmitate, glycerol trimyristate, glycerol tri-2-heptylundecanoate, castor oil fatty acid methyl ester, oleic acid oil, cetearyl alcohol, acetglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate; silicone derivatives including chain polysiloxanes, such as dimethyl polysiloxane, methylphenyl polysiloxane, and methylhydrogen polysiloxane, cyclic polysiloxanes, such as decamethyl polysiloxane, dodecamethyl polysiloxane, and tetramethyltetrahydrogen polysiloxane, silicone resins forming a three-dimensional network structure, and silicone rubber, anionic surface active agents, such as soap base, fatty acid soaps (e.g., sodium laurate or sodium palmitate), higher alkylsulfates (e.g., sodium lauryl sulfate and potassium lauryl sulfate), alkyl ether sulfates (e.g., POE triethanolamine lauryl sulfate and POE sodium lauryl sulfate), N-acylsarcosine (e.g., sodium lauroylsarcosine), higher fatty acid amide sulfonates (e.g., sodium N-myristoyl-N-methyltaurine, sodium coconut-oil fatty acid-methyltaurine, and sodium laurylmethyltaurin), phosphoric ester salts (e.g., sodium POE oleyl ether phosphate and POE stearyl ether phosphoric acid), sulfosuccinates (e.g., sodium di-2-ethylhexylsulfosuccinate, sodium monolauroylmonoethanolamide polyoxyethylene sulfosuccinate, and sodium lauryl polypropylene glycol sulfosuccinate), alkylbenzenesulfonates (e.g., sodium linear dodecylbenzenesulfonate, triethanolamine linear dodecylbenzenesulfonate, linear dodecylbenzenesulfonic acid), N-acylglutamates (e.g., sodium N-lauroylglutamate, disodium N-stearoylglutamate, and monosodium N-myristoyl-L-glutamate), higher fatty acid ester sulfates (e.g., sodium glycerol hardened coconut oil fatty acid sulfate), sulfated oils (e.g., Turkey red oil), POE alkyl ether carboxylic acids, POE alkyl allyl ether carboxylates, .alpha.-acid alkylolamidosulfates, sodium lauroyl monoethanolamidosuccinate, ditriethanolamine N-palmitoylaspartate, and casein sodium; cationic surface active agents, such as alkyltrimethylammonium salts (e.g., stearyltrimethylammonium chloride and lauryltrimethylammonium chloride), distearyldimethylammonium chloride, alkylpyridinium salts (e.g., poly(N,N'-dimethyl-3,5-methylenepiperidinium) chloride and cetylpyridinium chloride), alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride; amphoteric surface active agents, such as imidazoline type amphoteric surface active agents (e.g., sodium 2-undecyl-N,N,N-(hydroxyethylcarboxymethyl)-2-imidazoline and 2-cocoyl-2-imidazolinium hydroxide-1-carboxyethyloxy disodium), and betaine type amphoteric surface active agents (e.g., 2-heptadecyl-N-carboxymethyl-N-hydroxyethylimidazolinium betaine, lauryldimethylaminoacetic acid betaine, alkylbetaines, amidobetaines, and sulfobetaines; lipophilic nonionic surface active agents, such as sorbitan fatty acid esters (e.g., sorbitan mono-oleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate), glycerol fatty acid esters (e.g., glycerol mono-cotton seed oil fatty acid ester, glycerol monoerucate, glycerol sesquioleate, glycerol monostearate, glycerol .alpha.,.alpha.'-oleate pyroglutamate, and glycerol monostearate malate), propylene glycol fatty acid esters (e.g., propylene glycol monostearate), hardened castor oil derivatives, glycerol alkyl ethers, and polyoxyethylene-methyl polysiloxane copolymers; hydrophilic nonionic surface active agents, such as POE sorbitan fatty acid esters (e.g., POE sorbitan mono-oleate, POE sorbitan monostearate and POE sorbitan tetraoleate), POE sorbitol fatty acid esters (e.g., POE sorbitol monolaurate, POE sorbitol mono-oleate, POE sorbitol pentaoleate, and POE sorbitol monostearate), POE glycerol fatty acid esters (e.g., POE glycerol monostearate, POE glycerol monoisostearate, and POE glycerol triisostearate), POE fatty acid esters (e.g., POE mono-oleate, POE distearate, POE monodioleate, and ethylene glycol distearate), POE alkyl ethers (e.g., POE lauryl ether, POE oleyl ether, POE stearyl ether, POE behenyl ether, POE 2-octyldodecyl ether, and POE cholestanol ether), POE alkyl phenyl ethers (e.g., POE octyl phenyl ether, POE nonyl phenyl ether, and POE dinonyl phenyl ether), polyoxyethylene polypropylene glycol ether (e.g., Pluronic), POE-POP alkyl ethers (e.g., POE-POP cetyl ether, POE-POP 2-POP glycerol ether), tetra POE-tetra POP ethylenediamine condensates (e.g., Tetronic), POE castor oil or hardened castor oil derivatives (e.g., POE castor oil, POE hardened castor oil, POE hardened castor oil monoisostearate, POE hardened castor oil triisostearate, POE hardened-castor oil monopyroglutamate monoisostearate, and POE hardened castor oil maleate), POE molasses lanolin derivatives (e.g., POE sorbitol molasses), alkanolamides (e.g., coconut oil fatty acid diethanolamide, lauric monoethanolamide, and fatty acid isopropanolamide), POE propylene glycol fatty acid esters, POE alkylamines, POE fatty acid amides, sucrose fatty acid esters, POE nonylphenyl formamide condensate, alkylethoxydimethylamine oxides, and trioleyl phosphate; antiseptics such as methyl p-hydroxybenzoate, ethyl p-hydroxybenzoate, and butyl p-hydroxybenzoate; masking agents, such as disodium edetate and EDTA; naturally occurring water-soluble high polymers including vegetable high polymers, such as gum arabic, tragacanth, galactan, guar gum, carob gum, karaya gum, carrageenan, pectin, agar, quince seeds, algae colloid (brown algae extract), starch (rice, corn, potato or wheat), and glycyrrhizic acid, microorganism high polymers, such as xantham gum, dextran, succinoglucan, and pullulan, and animal high polymers, such as collagen, casein, albumin, and gelatin; semisynthetic water-soluble high polymers, such as starch high polymers (e.g., carboxymethyl starch and methylhydroxypropyl starch), cellulose high polymers (e.g., methyl cellulose, nitrocellulose, ethyl cellulose, methylhydroxypropyl cellulose, hydroxyethyl cellulose, sodium cellulose sulfate, hydroxypropyl cellulose, carboxymethyl cellulose (CMC) sodium, microcrystalline cellulose, and powdered cellulose), and alginic acid high polymers (e.g., sodium alginate and propylene glycol alginate); synthetic water-soluble high polymers, such as vinyl polymers (e.g., polyvinyl alcohol, polyvinyl methyl ether, polyvinylpyrrolidone, carboxyvinyl polymer (Carbopol), and alkyl-modified carboxyvinyl polymers), polyoxyethylene high polymers (e.g., polyethylene glycol 2000, 4000 or 6000), polyoxyethylene-polyoxypropylene copolymers, acrylic polymers (e.g., sodium polyacrylate, polyethyl acrylate, and polyacrylamide), polyethylene-imine, and cationic polymers; inorganic water-soluble high polymers, such as bentonite, magnesium aluminum silicate, laponite, hectorite, and silicic anhydride; thickeners, such as gum arabic, carrageenan, karaya gum, tragacanth, carob gum, quince seeds, casein, dextrin, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust beam gum, guar gum, tamarind gum, cellulose dialkyldimethylammonium sulfate, xantham gum, aluminum magnesium silicate, bentonite, sericite, commonmica, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (calcined gypsum), calcium phosphate, fluorapatite, hydroxyapatite, ceramic powder, metal soaps (e.g., zinc myristate, calcium palmitate and aluminum stearate), and boron nitride, and organic powders, such as polyimide resin powder (nylon powder), polyethylene powder, polymethyl methacrylate powder, polystyrene powder, styrene-acrylic acid copolymer resin powder, benzoguanamine resin powder, polytetrafluoroethylene powder, and cellulose powder, colorants, such as inorganic white pigments (e.g., titanium dioxide and zinc oxide), inorganic red pigments (e.g., iron oxide and iron titanate), inorganic brown pigments (e.g., .gamma.-iron oxide), inorganic yellow pigments (e.g., yellow iron oxide and ocher), inorganic black pigments (e.g., black iron oxide, carbon black, and titanium oxide of low order), inorganic purple pigments (e.g., mango violet and cobalt violet), inorganic green pigments (e.g., chromium oxide, chromium hydroxide, and cobalt titanate), inorganic blue pigments (e.g., ultramarine and Prussian blue), pearlescent pigments (e.g., titanium oxide-coated mica, titanium oxide-coated bismuth oxychloride, titanium oxide-coated talc, colored titanium oxide-coated mica, bismuth oxychloride, and fish scale guanine), metal powder pigments (e.g., aluminum powder and copper powder), organic pigments (e.g., Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404), zirconium, barium or aluminum lake organic pigments (e.g., Red. No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1), natural dyes (e.g., chlorophyll and beta-carotene), Titan Yellow, carthamin, and safflower, perfumes; water, alcohols; and the like.

The compositions of the present invention may be prepared by any conventional technique for preparing a cosmetic composition by merely substituting an aqueous extract from *Angelica sinensis* or a fraction or a lyophilizate thereof, or one or more active components contained in said extract for the water normally incorporated into the composition.

The present invention having been described in detail in the preceding sections, the following examples are provided to illustrate certain aspects of, but not to limit, the invention.

EXAMPLES

Example 1

Stimulatory Effect of SBD.4 Purified by DEAE on the Proliferation of Endothelial Cells This example illustrates the SBD.4 stimulation of bovine capillary endothelial (BCE) cell growth in a dose-dependant manner, in vitro. FIG. 1 demonstrates this effect with SBD.4 angiostimulatory extract purified by the means of filtration and DEAE-cellulose. Briefly, dried, fragmented roots of *Angelica sinensis* were placed in water (w:v=1:20), brought to boil and boiled for 30 minutes at 95 degrees centigrade. The aqueous extract was then cooled to room temperature, centrifuged to remove insoluble solids and sterile-filtered through a 0.22 micron Nalgene filter. This filtrate was passed through a centrifugal filter device (Millipore) of 10,000 daltons molecular weight cut-off and the angiostimulatory material was collected in the lower chamber. Thirty-five milliliters of this angiostimulatory material was then applied to 8 centimeters×1 centimeter DEAE column.

The angiostimulatory activity was eluted by the aqueous solution of five hundred millimolar (mM) sodium chloride with one hundred millimolar hydrochloric acid. The flow rate through the column during the whole process was 2 milliliter/minute.

The angiostimulatory material eluted from the DEAE column was tested on the proliferation of bovine capillary endothelial cells in 96 well tissue culture plate. Cells were plated at about 3,000 cells per well in DMEM medium (Hyclone, South Logan, Utah) supplemented by 5% of bovine calf serum (Hyclone, South Logan, Utah). The following day three different concentrations of SBD.4 eluted from the DEAE column were added to cells (final concentrations: 0.5 microgram per milliliter (µg/ml), 2 µg/ml and 10 µg/ml). One nanogram per milliliter (ng/ml; final concentration) of bFGF was added to other wells as control. Cells were counted seventy-two hours later. Cell number was estimated using the sulforhodamine B (Sigma, St. Louis, Mo.) colorimetric assay (Skehan et al., 1990) The results were graphically represented, with the number of cells represented as optical density (OD) readings at 570 nanometers wavelength of sulforhodamine B staining, plotted on the Y axis (see FIG. 1). The extent of this stimulation is comparable with bFGF, which is a major angiostimulatory factor in humans. The mechanism of action of SBD.4 may involve the stimulation of the bFGF and/or VEGF production and/or binding to endothelial cells and/or interference with the nitric oxide pathways.

Example 2

SBD.4 Stimulates Proliferation of Capillary Endothelial Cells, and Vessel-Like Structure Formation in a Tri-Dimensional Model by SBD.4

As shown in the FIG. 2, HPLC-purified SBD.4 strongly stimulates another batch of capillary endothelial cells (compare "Control" and "SBD.4" bars). Furthermore, this figure shows that SBD.4 is significantly more stable at room temperature than basic fibroblast growth factor (bFGF), and unlike bFGF, it is pronase-insensitive (compare "SBD.4 (RT)" with "bFGF(RT)" and "SBD.4/Pronase" with "bFGF/Pronase".

It is known in the art that pronase is a potent combination of several endo- and exo-proteinases, which can cleave almost any peptide bond. These results suggest that SBD.4 may maintain its activity in the proteolytic environment of the wound to much greater extent than proteinaceous growth factors tested for wound healing, such as bFGF and PDGF (platelet derived growth factor).

Figure 3A:
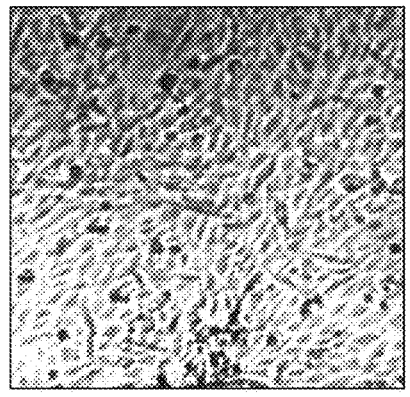
Figure 3B:
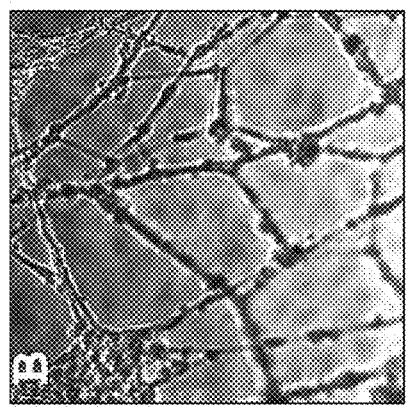
Figure 3C:
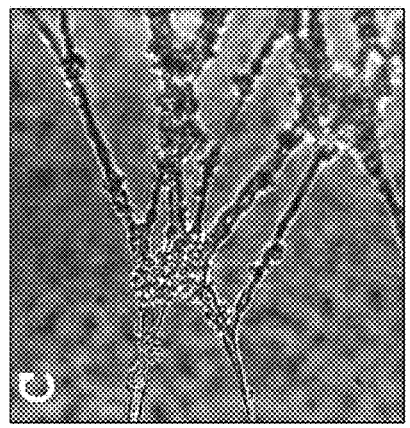

As demonstrated in FIG. 3, SBD.4 (purified by DEAE and HPLC) is also capable of inducing capillary-like structures in a tridimensional tube formation model developed in our laboratory. In this model, capillary-like structures are induced by plating bovine endothelial cells (about 8000 cells per well) in a 96 well tissue culture-treated plate (Costar) in DMEM supplemented with 5% calf serum (Hyclone, Logan, Utah), with or without an endothelial cell stimulatory growth factor. Cells cultured for 2-5 weeks with such a stimulatory growth factor (for example bFGF, FIG. 3C) form capillary-like structures. Cells grown without such factor form a monolayer (FIG. 3A).

This example shows that SBD.4 (5 µml; FIG. 3B) induces a remodeling response, leading to the generation of a tridimensional network of vessel-like structures, similar to, and often more complete than the one induced by the optimal concentration of bFGF (15 ng/ml, or nanograms/milliliter, FIG. 3C), used as positive control.

Example 3

SBD.4 Stimulates Angiogenesis In Vivo, in the Chorioallantoic Membrane (CAM) Assay The chorioallantoic membrane (CAM) is a highly vascularized structure present in fertilized, developing hen egg. The sensitive, semi-quantitative assay using CAM has been used for testing many angiogenesis inhibitors and stimulators (Ribatti et al., 2000). The assay consists of placing a methylcellulose pellet containing the compound of interest on the CAM of an 8 day-old chick fertilized egg grown in a Petri dish. The compound (in our case SBD.4) is gradually released from the pellet and its effect on the embryo vasculature (induction of new blood vessels) is assessed optically. FIG. 4 illustrates the result of 3 kD cut off filtration-purified SBD.4 on the vascularization in this assay. When a methylcellulose pellet with SBD.4 is placed on the CAM (in the center of the panel A; it is hardly visible, because it is transparent), one can observe generation of several new blood vessel growing towards the pellet as early as 24 hours (24 h) later (note for example a hook-like red capillary sprouting from the preexisting vessel in the center of the panel B). Panel C illustrates a typical "spokes of a wheel" pattern of new blood vessels converging towards the pellet with *Angelica* (darker area in the center of the panel C) 48 hours (48 h) after the beginning of a different experiment. Together, these experiments demonstrate the angiostimulatory potential of SBD.4 in this in vivo system.

Example 4

Stimulatory Effect of SBD.4 on Human Dermal Fibroblasts

Figure 5B:
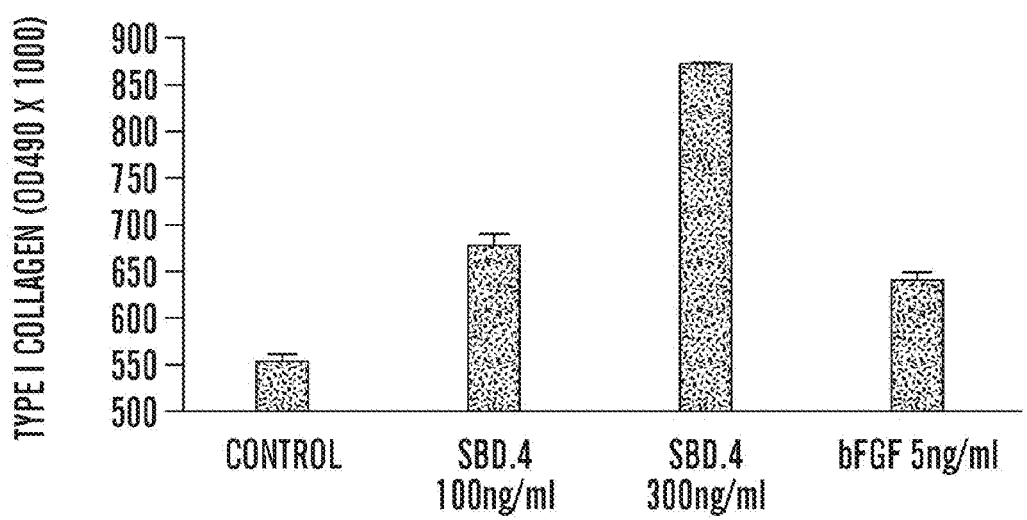

This example shows that DEAE- and HPLC-purified SBD.4 has a stimulatory effect on human dermal fibroblasts and on type I collagen output. Human neonatal dermal fibroblasts (passage 3-5; Cambrex, Walkersville, Md.) were cultured at 5% $CO_2$ in complete fibroblast growth medium (FGM-2 bulletkit; Cambrex cat.# CC-3132). After 3 days this medium was replaced. 0.05% glucose (negative control) or SBD.4 was added to cells, which were then incubated one week. At the end of the experiment, cell number was determined by a colorimetric method, according to Skehan and coll. (1990). We found that nanogram amounts of SBD.4 stimulated human dermal fibroblast growth (FIG. 5A) and collagen I concentration in fibroblast-conditioned medium (FIG. 5B). Longer periods of incubation at suboptimal conditions (for example 1 month) resulted in even bigger differences in cell number and collagen output between controls and SBD.4-treated cells, in favor of the latter.

Example 5

SBD.4 Enhances Wound Closure in Diabetic Mice

We have chosen to use the genetically diabetic mice (13 week old female BKS Cg-m +/+ Lepr(db), stock # 642, Jackson Labs) because it is an optimal model reflecting the impaired wound healing in a segment of the population particularly vulnerable to chronic wounds—the diabetic patients. This genetically diabetic mouse model is well established as documented by over 50 publications (for example see Tsuboi et al., 1992). Many companies have also used it as a standard pre-clinical model, including Johnson & Johnson, which included it in the pre-clinical data package submitted to FDA as part of their IND application for becaplermin.

Two concentrations of saline solutions of SBD.4 (3 kd cut-off filtered aqueous extract): 10 mg per wound and 2 mg per wound (20 $mg/cm^2$, and 4 $mg/cm^2$, respectively) against saline (PBS) as negative control. The concentrations of SBD.4 have been based on the fact that there is a 3 to 4 log difference between the concentration of bFGF required for the stimulation of endothelial cells in vitro and the bFGF concentration active in diabetic mouse wounds (Greenhalgh et al., 1990). Thus, we also chose this multiplication factor for our angiostimulator.

Twelve mice were divided in 2 groups and 8 mm (diameter) full thickness excisional wounds were performed under anesthesia on each side of the animal with a punch biopsy tool and covered by sterile gauze (occlusive dressings were not used as they considerably delay wound healing, according to the experience of the Principal Inventor and to the published reports (Lasa et al., 1993). The number of animals per group was based on the previous publications with this model; Jacobi et al., 2002). In Group 1 (the experimental treatment group), one wound on each animal was treated by 50 ul of "high" concentration of SBD.4 (10 mg per wound) and the other one by 50 ul of "low" concentration of SBD.4 (2 mg per wound). In Group 2 (negative control), both wounds were treated by PBS (phosphate buffered saline). Treatments were applied on the first day and every second day thereafter. Wound surface were measured every second day. Wound closure was determined by the following formula: percent closure={(area on day 0–open area)/area on day 0}×100. Wounds were considered closed if moist granulation tissue was no longer apparent, and the wound appeared covered with new epithelium.

All mice survived until the end of the experiment. However, the wounds of one control mouse refused to heal through the course of the experiment. This was in contrast with other control mice, whose wounds slowly progressed towards healing. Therefore, the control mouse with non-healing wounds has been excluded from the computational evaluation. As shown in Table I, both concentrations of SBD.4 stimulated wound closure, compared to the negative control. There was no significant advantage in using 10 mg over 2 mg of the product per wound. Therefore, 2 mg SBD.4 per wound has been chosen for further experiments.

TABLE I

Median percentage of wound closure in genetically diabetic mice. Wounds were treated by 10 mg SBD.4 (High SBD.4); 2 mg SBD.4 (Low SBD.4) or by PBS (control). The overall stimulation by low and high concentrations of SBD.4 was comparable, and thus the lower dose was chosen for further studies. The results were expressed as medians, as this representation is more statistically significant for small data sets (6 mice treated with SBD.4 and 5 controls - one control mouse has been removed from the set due to non-healing wounds).

|    | (% wound closure) | (% wound closure) | SBD.4 (% wound closure) | SBD.4 relative to Control (control = 1) | SBD.4 relative to Control (control = 1) |
|----|-------------------|-------------------|--------------------------|------------------------------------------|------------------------------------------|
| 1  | 0                 | 0                 | 0                        | —                                        | —                                        |
| 3  | 30                | 32.11             | 34.6                     | 1.07                                     | 1.153                                    |
| 5  | 35.3              | 48                | 43.3                     | 1.36                                     | 1.227                                    |
| 6  | 38.8              | 51                | 54.9                     | 1.314                                    | 1.415                                    |
| 8  | 51.2              | 73.4              | 68.8                     | 1.434                                    | 1.344                                    |
| 10 | 75                | 88                | 89.5                     | 1.173                                    | 1.193                                    |

Example 6

SBD.4 Enhances Wound Closure Better than Becaplermin in Diabetic Mice

This example illustrates the wound-healing stimulatory activity of the optimal (in the limits determined in Example 5) concentration of SBD.4. Also, in this experiment we compared the bioactivity of 3 kD cutoff filter-purified SBD.4 to becaplermin (Regranex, Johnson & Johnson; the positive control).

Twelve mice were divided in two groups and two wounds per mouse were effectuated as in Example 5. In order to exclude the possibility of mouse-to-mouse variability in wound healing, in this experiment every mouse was treated by the test sample on one wound and by PBS (negative control) on another wound. Thus, one group of 6 mice was treated with 50 ul of SBD.4 (2 mg/wound) on one wound, and by 50 ul of PBS on the other wound, while the second group of 6 mice was treated with becaplermin (positive control; 5 ug in 50 ul CMC—carboxymethylcellulose—gel) on one and PBS on another wound. The concentration of becaplermin was based on the dose used by Johnson & Johnson in their preclinical studies (2) and on published studies with PDGF-B, in the db/db model (Greenhalgh et al., 1990).

Treatments were applied on the first day and every second day thereafter. Wound surface were measured every second day. Wound closure for each wound was determined by the formula: percent closure={(area on day 0–open area)/area on day 0}×100. Wounds were considered closed if moist granulation tissue was no longer apparent, and the wound appeared covered with new epithelium. The dynamics of wound closure for the 2 groups is plotted on FIG. 6 (means) and Table II (medians). Both representations show a significant stimulation of wound closure by SBD.4 as compared with the negative control (PBS). This stimulation is superior to the effect achieved with becaplermin.

Example 7

SBD.4 Enhances Wound Closure 1N Human/SCID Mouse Chimera Model

Materials and Methods

Human skin graft in severe combined immunodeficient (SCID) mice is a powerful model for evaluating the effect of wound-healing drug-candidates on full-thickness wounds (Juhasz et al., 1993). The wound model in human skin/SCID chimera features normal migration of neutrophils and macrophages to the wound bed, as well as normal expression of growth factors associated with wound-healing, and therefore provides a good approximation of human dermal wound-healing process (Matsumoto et al., 1997). The disadvantage of this model is that it is delicate to handle and time-consuming. The donor skin must be immediately placed on ice and taken to the lab, where a 10-hour grafting procedure follows. We used surgical waste skin obtained under informed consent from a patient undergoing abdominoplasty.

TABLE II

Median percentage of wound closure. Wounds were treated by 2 mg SBD.4; 5ug becaplermin or by PBS (control). There was a strong, consistent stimulation of wound closure by SBD.4. The positive control (Becaplermin) also stimulated closure, however, the stimulation by SBD.4 was significantly stronger.

| Day | Control (% closure) | SBD.4 (% closure) | Becaplermin (% closure) | Stimulation by SBD.4 relative to Control (control = 1) | Stimulation by becaplermin relative to Control (control = 1) |
|---|---|---|---|---|---|
| 1 | 0 | 0 | 0.0 | — | — |
| 3 | 1.6 | 13.0 | 1.7 | 8.1 | 1.1 |
| 5 | 28.5 | 47.6 | 11.9 | 1.7 | 0.4 |
| 7 | 36.3 | 58.1 | 41.2 | 1.6 | 1.1 |
| 9 | 51.5 | 89 | 65.8 | 1.7 | 1.3 |
| 11 | 66.0 | 97.9 | 86.7 | 1.5 | 1.3 |

Controls: n = 12;
SBD.4: n = 6,
Becaplermin: n = 6.

After 6 weeks, when the graft anastomosed with the murine skin 8 mm (diameter) full thickness wounds were excised in the human skin. Mice received treatment (ointment every two days) of either becaplermin (Regranex, positive control), 2% carboxymethylcellulose (CMC, negative control) or SBD.4 in 2% CMC on the day of wounding and every second day thereafter. Initial wound closure (defined by the coverage of the base of the wound with bridging granular tissue and new epithelium) was assessed every 3 days.

Results and Discussion:

As shown in Table III, there was a dramatic increase in the initial wound closure in mice treated by SBD.4. On day 6, in the control group, none of the wounds was closed. In contrast, in the SBD.4 group, all wounds were closed. Control wounds (PBS-treated) achieved the same ratio of closure only at day 16.

TABLE III

Initial wound closure (defined as presence of bridging tissue, no moist granulation tissue, epithelialization) on day 6 in human grafts treated with PBS (negative control), becaplermin (positive control) and SBD.4.

| # animals showing initial wound closure on: | Group: | | |
|---|---|---|---|
| | Control (PBS) | Becaplermin | SBD.4 |
| Day 3 | 0/5 | 0/5 | 0/5 |
| Day 6 | 0/5 | 1/5 | 5/5 |
| Day 9 | 1/4 | 2/4 | 4/4 |
| Day 12 | 2(3?)/4 | 4/4 | 4/4 |
| Day 16 | 4/4 | 4/4 | 4/4 |

On Day 6, all wounds in SBD.4-treated animals were closed, only one wound in the Regranex (becaplermin) group was closed and no vehicle (CMC)-treated wounds were closed. N = 5 for all groups until day 6, when 1 representative mouse from each group was sacrificed.
N = 4 for days 7-16.

Skin was defatted (if it is not well defatted, the remaining adipose tissue easily undergoes necrosis, which interferes with graft taking. But on the other side, removing the underlying fat tissue too slowly or too zealously can also damage the skin and compromise the graft), and grafted (2.5×2.5 cm) on 15 SCID mice (Charles River Labs), using 10-12 stitches per graft. Here, the challenge is to suture the thick human skin with the much thinner rodent tissue.

Example 8

Composition of SBD.4 at Three Representative Levels of Purity

This example shows the composition of SBD.4 at successive stages of purification, as visualized by HPLC-MS (FIG. 7). The endothelial- and fibroblast-stimulatory activity of SBD.4 is retained as the number of molecular entities is reduced from multiple in the aqueous extract purified by molecular weight cut-off filtration (FIG. 7A-B), to less than 10 in the same extract further purified by reverse phase HPLC (FIG. 7C-D). This number is further reduced when HPLC is preceded by DEAE-cellulose chromatography followed by methanol precipitation (FIG. 7E-F). The most far-right peak on panels 7C and 7D is an impurity coming from the column and is not part of SBD.4.

REFERENCES

Dobak J, Grzybowski J, Liu F T, Landon B, Dobke M (1994) 1,25-Dihydroxyvitamin

Greenhalgh D G, Sprugel K H, Murray M J, Ross R. PDGF and FGF stimulate wound healing in the genetically diabetic mouse. Am J Pathol. 1990 June; 136(6):1235

Jacobi J, Jang J J, Sundram U, Dayoub H, Fajardo L F, Cooke J P. Nicotine accelerates angiogenesis and wound healing in genetically diabetic mice. Am J Pathol. 2002, 161:97

Juhasz I, Murphy G F, Yan H C, Herlyn M, Albelda S M. Regulation of extracellular matrix proteins and integrin cell substratum adhesion receptors on epithelium during cutaneous human wound-healing in vivo. Am. J. Pathol. 1993; 143:1458

Laham R J, Chronos N A, Pike M, Leimbach M E, Udelson J E, Pearlman J D, Pettigrew R I, Whitehouse M J, Yoshizawa C, Simons M. Intracoronary basic fibroblast growth factor (FGF-2) in patients with severe ischemic heart disease: results of a phase I open-label dose escalation study. J Am Coll Cardiol. 2000 36:2132

Lasa C I Jr, Kidd R R 3rd, Nunez H A, Drohan W N. Effect of fibrin glue and opsite on open wounds in DB/DB mice. J Surg Res. 1993 54:202

Matsumoto K, Robb E, Warden G, Nordlund J. The expression of cytokines, growth factors and ICAM-1 in the healing of human cutaneous xenografts on nude mice. Exp. Dermatol. 1997; 6:13

Ribatti D, Vacca A, Roncali L, Dammacco F. The chick embryo chorioallantoic membrane as a model for in vivo research on anti-angiogenesis. Curr Pharm Biotechnol. 2000 1:73

Skehan P, Storeng R, Scudiero D, Monks A, McMahon J, Vistica D, Warren J T, Bokesch H, Kenney S, Boyd M R. New colorimetric cytotoxicity assay for anticancer-drug screening. J. Natl. Cancer Inst. 1990; 82:1107

Tsuboi R, Shi C M, Rifkin D B, Ogawa H. A wound healing model using healing-impaired diabetic mice. J Dermatol. 1992 19:673

The invention claimed is:

1. A method of enhancing healing or appearance of mammalian dermal tissue comprising:
   contacting said dermal tissue with a composition comprising an effective amount of an *Angelica sinensis* extract, wherein said *Angelica sinensis* extract is produced by a process comprising the step of:
   providing roots or root material of *Angelica sinensis*;
   extracting said roots or root material in an aqueous solution selected from the group consisting of water, aqueous alcohol, aqueous polar solvents, and combinations thereof, thus forming an aqueous extract;
   filtering said aqueous extract through a device with molecular cut-off weight of 3,000 Daltons to 10,000 Daltons; and collecting the filtered aqueous extract.

2. The method of claim 1, wherein said composition is a pharmaceutically acceptable composition further comprising a pharmaceutically acceptable diluent or carrier.

3. The method of claim 1, wherein said composition is a cosmetic composition.

4. The method of any of claim 1, wherein said filtering is through a device with molecular cut-off weight of 10,000 Daltons, 5,000 Daltons, or 3,000 Daltons.

5. The method of claim 1, wherein the extracting step is carried out at room temperature to boiling.

6. The method of claim 1, wherein said filtered aqueous extract is further purified by column chromatography to obtain a purified extract in which compounds having a molecular weight of 700 Daltons or greater are removed therefrom.

7. The method of claim 1, wherein said aqueous extract is also filtered through a filter having a pore size of 0.22 microns.

8. The method of claim 1, wherein said composition is attached to a backing.

9. The method of claim 8, wherein said backing is an adhesive medical tape.

10. The method of claim 8, wherein said backing comprises a porous material, non-porous, or micro-porous material.

11. The method of claim 1, wherein said composition further comprises an agent for treatment or management of wounds.

12. The method of claim 11, wherein said agent is selected from the group consisting of dexpanthenol, growth factors, enzymes, hormones, povidon-iodide, fatty acids, antibiotics, antimicrobials, analgesics, antiseptics, collagens, celluloses, gelatin, and any combinations thereof.

13. The method of claim 12, wherein said growth factor is selected from the group consisting of fibroblast growth factors (FGF), FGF-1, FGF-2, FGF-4, thymosins, platelet-derived growth factors (PDGF), insulin binding growth factors (IGF), IGF-1, IGF-2, epidermal growth factor (EGF), transforming growth factor (TGF), TGF-alpha, TGF-beta, cartilage inducing factors-A and -B, osteoid-inducing factors, osteogenin, bone morphogenic proteins and other bone growth factors, collagen growth factors, heparin-binding growth factor-1 or 2, biologically active analogs and derivatives thereof, and any combinations thereof.

14. The method of claim 1, wherein said composition further comprises a compound selected from the group consisting of oils, antioxidants, preservatives, non-occlusive moisturizers, humecantants, gelling agents, neutralizing agents, perfumes, coloring agents, surfactants, keratolytic agents, UV absorbing and/or screening agents, whitening agents, anti-inflammatory agents, collagens, celluloses, gelatin, skin soothing agents, plant extracts, vitamins, minerals, and any combinations thereof.

15. The method of claim 1, wherein said composition is a hydrogel, lotion, cream, shampoo, cleanser, or make-up foundation.

* * * * *